US010287336B2

(12) United States Patent
Lu et al.

(10) Patent No.: US 10,287,336 B2
(45) Date of Patent: May 14, 2019

(54) FELINE ERYTHROPOIETIN RECEPTOR AGONISTS

(71) Applicant: AskGene Pharma, Inc., Camarillo, CA (US)

(72) Inventors: Jian-Feng Lu, Oak Park, CA (US); Yuefeng Lu, Newbury Park, CA (US); Aijun Wang, Camarillo, CA (US); Donggou He, Camarillo, CA (US); Kurt Shanebeck, Camarillo, CA (US); Chen Yao, Moorpark, CA (US)

(73) Assignee: AskGene Pharma, Inc., Camarillo, CA (US)

( * ) Notice: Subject to any disclaimer, the term of this patent is extended or adjusted under 35 U.S.C. 154(b) by 0 days.

(21) Appl. No.: 14/857,799

(22) Filed: Sep. 17, 2015

(65) Prior Publication Data

US 2016/0083444 A1   Mar. 24, 2016

Related U.S. Application Data

(60) Provisional application No. 62/052,407, filed on Sep. 18, 2014.

(51) Int. Cl.
*C07K 14/505* (2006.01)
*A61K 38/00* (2006.01)
*C12N 15/62* (2006.01)

(52) U.S. Cl.
CPC ............ *C07K 14/505* (2013.01); *A61K 38/00* (2013.01); *C07K 2319/30* (2013.01)

(58) Field of Classification Search
None
See application file for complete search history.

(56) References Cited

U.S. PATENT DOCUMENTS

| 7,217,689 | B1 * | 5/2007 | Elliott | C07K 14/505 435/320.1 |
|---|---|---|---|---|
| 2006/0228332 | A1 | 10/2006 | Gillies et al. | |
| 2007/0190610 | A1 * | 8/2007 | Fares | C07K 14/505 435/69.1 |
| 2009/0029907 | A1 * | 1/2009 | Patell | C07K 14/505 514/1.1 |
| 2009/0238789 | A1 * | 9/2009 | Guyon | A61K 31/555 424/85.2 |
| 2010/0093608 | A1 * | 4/2010 | Tian | C07K 14/505 514/1.1 |
| 2011/0002917 | A1 * | 1/2011 | Hansen | C07K 16/18 424/133.1 |
| 2011/0256586 | A1 * | 10/2011 | Egrie | C07K 14/505 435/69.1 |
| 2012/0264686 | A9 | 10/2012 | Guyon et al. | |

FOREIGN PATENT DOCUMENTS

EP  0640619 A1  3/1995

OTHER PUBLICATIONS

Boissel et al. Erythropoietin structure-function relationships. Mutant proteins that test a model of tertiary structure. The Journal of Biological Chemistry, vol. 268, No. 21:15983-15993 (1993).*
Chern et al. Structural role of amino acids 99-110 in recombinant human erythropoietin. European Journal of Biochemistry, vol. 202:225-229 (1991).*
Mitra et al. N-linked oligosaccharides as outfitters for glycoprotein folding, form and function. TRENDS in Biochemical Sciences, vol. 13 No. 3:156-163 (2006).*
Imai et al. Physicochemical and biological characterization of asialoerythropoietin. Suppressive effects of sialic acid in the expression of biological activity of human erythropoietin in vitro. European Journal of Biochemistry 194:457-462 (1990).*
Wen et al. Erythropoietin Structure-Function Relationships: High Degree of Sequence Homology Among Mammals, Blood, Sep. 1, 1993, vol. 82, No. 5, pp. 1507-1516.
PCT/US15/50825 International Search Report and Written Opinion, dated Mar. 1, 2016.

* cited by examiner

Primary Examiner — Elizabeth C. Kemmerer
Assistant Examiner — Regina M DeBerry
(74) Attorney, Agent, or Firm — Entralta P.C.; Peter D. Weinstein; James W. Collett

(57) ABSTRACT

The present specification discloses erythropoietin receptor agonists, compositions and medicaments comprising such erythropoietin receptor agonists, methods and uses for such erythropoietin receptor agonists and compositions and medicaments, and methods and uses for erythropoietin receptor agonists and compositions and medicaments for treating an anemia.

7 Claims, 4 Drawing Sheets
Specification includes a Sequence Listing.

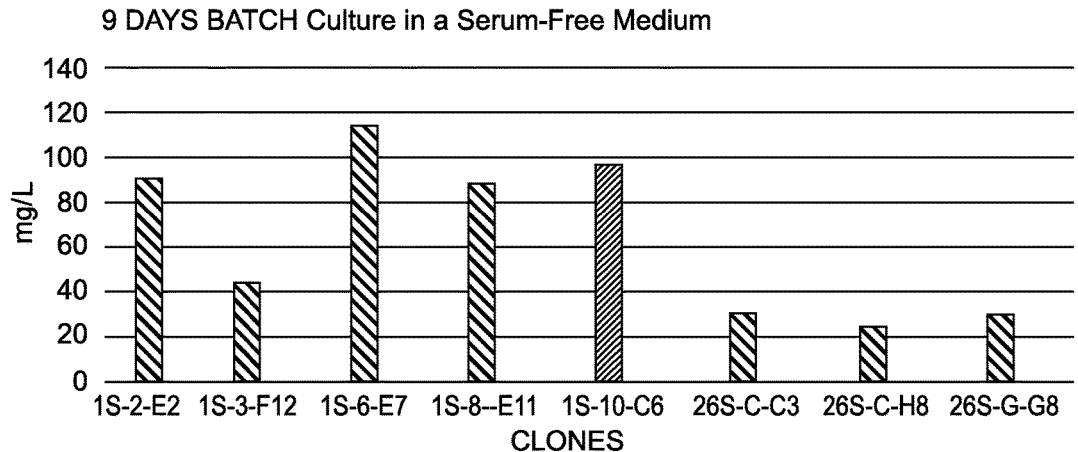
Fig. 3
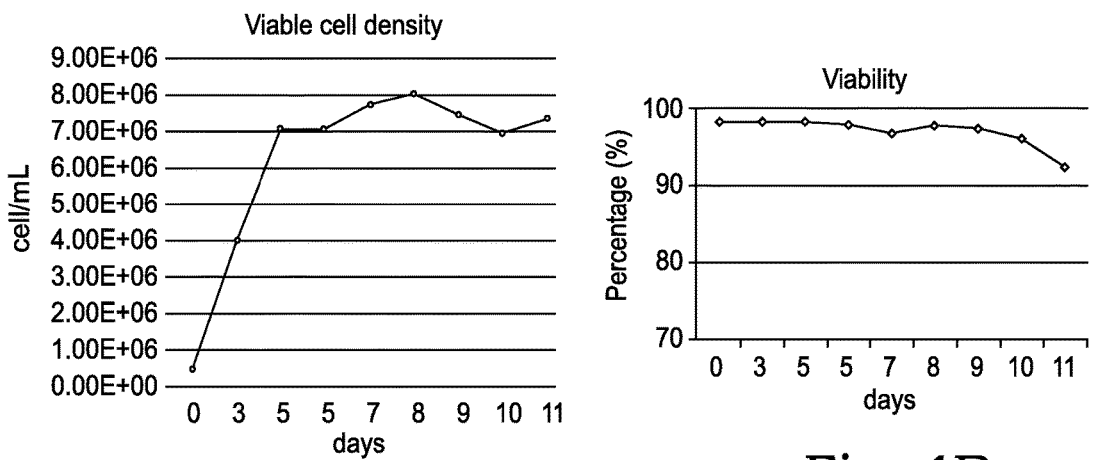
Fig. 4A
Fig. 4B
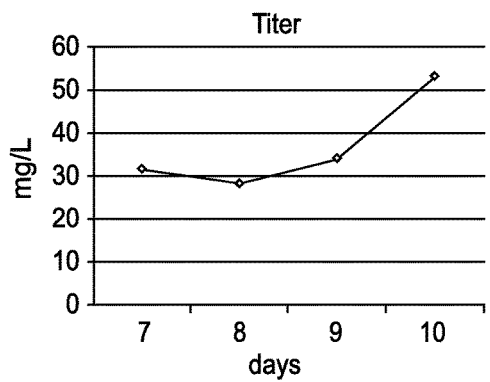
Fig. 4C

FELINE ERYTHROPOIETIN RECEPTOR AGONISTS

CROSS-REFERENCES TO RELATED APPLICATIONS

This patent application claims the right of priority pursuant to 35 U.S.C. § 119(e) and is entitled to the benefit of the filing date of U.S. Provisional Patent Application 62/052,407, filed on Sep. 18, 2014, the content of which is hereby expressly incorporated by reference in its entirety.

REFERENCE TO SEQUENCE LISTING

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows: File Name: SEQLIST-3IPAG3-0003US; Date of Creation: Sep. 15, 2014; Size (bytes): 17 KB

INTRODUCTION

Non-regenerative anemia (NRA) is a serious disease in cats, dogs and other mammals and there are no adequate therapies. Erythropoietin (EPO) is a glycoprotein hormone and is the most important hormone regulating erythropoiesis (red blood cell production). Recombinant human EPO products such as the non-glycosylated EPOGEN® and the glycosylated ARANESP® (Darbepoetin) have been commercially available to treat NRA in human. Human EPO is a heavily glycosylated protein with a molecular mass of 30.4 kD. The 5 exons of the EPO gene encode 193 amino acids, 27 of which are later cleaved off to produce a 166 amino acid long peptide, although the circulating peptide contains 165 amino acids. Its mature, circulating, structure includes a 165-amino acid backbone with three N-linked carbohydrates attached to asparagines at amino acid positions 24, 38, and 83 and one O-linked carbohydrate attached to $Ser^{126}$. Sixty percent of the EPO molecular mass is contributed by the 165 amino acids and 40% is contributed by the carbohydrate. The carbohydrates probably cover much of the surface of the molecule since they have extended and flexible structure.

The carbohydrate residues allow for many possible isoforms and contribute significantly to the serum half-life and biological activity of the hormone in vivo. The isoforms with increased sialic acid content have longer serum half-life and reduced receptor binding affinity. For EPO, the serum half-life is the primary determinant of in vivo activity. Darbepoetin was created through site directed mutation of two amino acid residues, allowing for two additional N-linked carbohydrate chains. The relative serum half-life, receptor binding affinity and biological activity are illustrated in FIG. 1.

It is estimated that there are over 0.5-1 million of domestic cats with NRA in US. Based on a veterinary survey, a number of conditions are associated with and/or can lead to NRA in cats including chronic renal failure (51%), cancer (16%), retroviral disease (11%), hyperthyroidism (5%), inflammatory bowel disease (4%), as well as other miscellaneous chronic conditions (6%) or multiple miscellaneous conditions (6%). Similar to human, chronic renal diseases and cancers are two main causes of NRA.

There is currently no adequate treatment for NRA in cats. Internal surveys have indicated that currently available treatments for NRA include EPOGEN® or other non-glycosylated human recombinant EPO (39%), the glycosylated recombinant EPO ARANESP® (5.7%), corticosteroids (32.5%), blood transfusions (6.7%), anabolic steroids (1.4%), as well as other miscellaneous treatments (5.3%). However, antibodies often developed in some of the cats against those human proteins, which resulted in serious conditions including pure red-cell aplasia (PRCA) in 25-30% of cats. ARANESP® may have low occurrence of PRCA in cats, estimated to be less than 10%, which is still significant. The second most frequently used option is steroids, which often result in serious side effects and dubious therapeutic efficacy. Blood transfusion is inconvenient and expensive. Thus, there is currently a serious unmet veterinary need for cats.

No species-specific EPO is commercially available for cat as of today. Feline EPO is only about 83% similar to that of the human EPO. Recombinant feline EPO was produced and tested in cats. Unfortunately, development of red cell aplasia was observed at a similar rate as that of recombinant human EPO. Thus, the addition of unmodified recombinant feline EPO would not address this unmet veterinary need.

Peptide-based erythropoietin receptor (EpoR) agonists have also been developed, such as disclosed in U.S. Pat. No. 6,703,480. In a small clinical trial, a peptide-based EpoR agonist was also shown to be effective for red cell aplasia in human. It is believed that the peptide-based EpoR agonist would not induce red cell aplasia as it does not share any sequence similarities to that of EPO. However, no studies have been reported using the peptide-based EpoR agonist in veterinary applications. In addition, hypersensitivity was also reported in a small number of patients using the pegylated peptide-based EpoR.

Present specification discloses novel EpoR agonists for cats, dogs and other mammals. In one embodiment, modifications are carried out on feline EPO to add one, two, three and/or more N-linked glycosylation sites, which allow for lower immunogenicity and higher serum half-life comparing to that of the feline EPO or human EPO. In another embodiment, peptide EpoR agonists are fused to feline IgG Fc to form fusion proteins, which are safe and effective in treating cat NRA.

SUMMARY

Aspects of the present specification disclose a modified non-human mammalian erythropoietin. The disclosed modified non-human mammalian erythropoietin is modified by adding or relocating at least one glycosylation site. The disclosed modified non-human mammalian erythropoietin may be a feline erythropoietin or a canine erythropoietin or a variant thereof. The added or relocated glycosylation site may be located at the carboxy terminal region of the mammalian erythropoietin or inserted between amino acids located in the mammalian erythropoietin sequence. A disclosed modified non-human mammalian erythropoietin may further comprise a fragment of human chorionic gonadotropin and/or at least one additional carbohydrate chain attached to a disclosed modified non-human mammalian erythropoietin.

Other aspects of the present specification disclose a nucleic acid sequence encoding a disclosed modified non-human mammalian erythropoietin as well as vectors comprising such nucleic acid sequences and hosts containing such vectors.

Other aspects of the present specification disclose a composition comprising a disclosed modified non-human mammalian erythropoietin. Such compositions further comprise one or more pharmaceutically acceptable diluents, adjuvants, or carriers.

Other aspects of the present specification disclose a use of a disclosed modified non-human mammalian erythropoietin in the manufacture of a medicament for the treatment of non-regenerative anemia (NRA).

Other aspects of the present specification disclose a method of treating non regenerative anemia (NRA) in a mammal. A method of treating disclosed herein comprising administering to a subject in need thereof an effective amount of a disclosed modified non-human mammalian erythropoietin. The treated mammal may be a cat, a dog, a mouse, a rat, a hamster, a rabbit, a guinea pig, a ruminant, a ferret, a non-human primate, or a pig.

Other aspects of the present specification disclose a use of a disclosed modified non-human mammalian erythropoietin for the treatment of non-regenerative anemia (NRA).

Other aspects of the present specification disclose a fusion protein, comprising a peptide, a linker and an Fc fragment where the peptide is fused through the linker to the Fc fragment. A disclosed peptide may be one having an amino acid sequence having at least 70% sequence identity to SEQ ID NO: 1, a feline EPO with the amino acid sequence SEQ ID NO: 5, a sequence having at least 70%, sequence identity to SEQ ID NO: 5, a modified feline EPO with the amino acid sequence SEQ ID NO: 6, or at least 70% sequence identity to SEQ ID NO: 6. A disclosed Fc fragment has an amino acid sequence of SEQ ID NO: 2, SEQ ID NO: 3 or SEQ ID NO: 4, or a sequence having at least 70% sequence identity to SEQ ID NO: 2, SEQ ID NO: 3 or SEQ ID NO: 4. The C terminus of the peptide may be fused through the linker to the N terminus of the Fc fragment or the N terminus of the peptide may be fused through the linker to the C terminus of the Fc fragment.

Other aspects of the present specification disclose a nucleic acid sequence encoding a disclosed fusion protein as well as vectors comprising such nucleic acid sequences and hosts containing such vectors.

Other aspects of the present specification disclose a composition comprising a disclosed fusion protein. Such compositions further comprise one or more pharmaceutically acceptable diluents, adjuvants, or carriers.

Other aspects of the present specification disclose a use of a disclosed fusion protein in the manufacture of a medicament for the treatment of non-regenerative anemia (NRA).

Other aspects of the present specification disclose a method of treating non-regenerative anemia (NRA) in a mammal. A method of treating disclosed herein comprising administering to a subject in need thereof an effective amount of a disclosed fusion protein. The treated mammal may be a cat, a dog, a mouse, a rat, a hamster, a rabbit, a guinea pig, a ruminant, a ferret, a non-human primate, or a pig.

Other aspects of the present specification disclose a use of a disclosed fusion protein for the treatment of non-regenerative anemia (NRA).

BRIEF DESCRIPTION OF THE DRAWINGS

a peptide disclosed herein is fused to the N-terminals or the C-terminals of the Fc domain FIG. 3 shows results of a batch culture of clones.

FIG. 4A shows a viable cell density graph over time; FIG. 4B shows a percent viability graph over time; and FIG. 4C shows titer levels over time.

DETAILED DESCRIPTION

Figure 1:
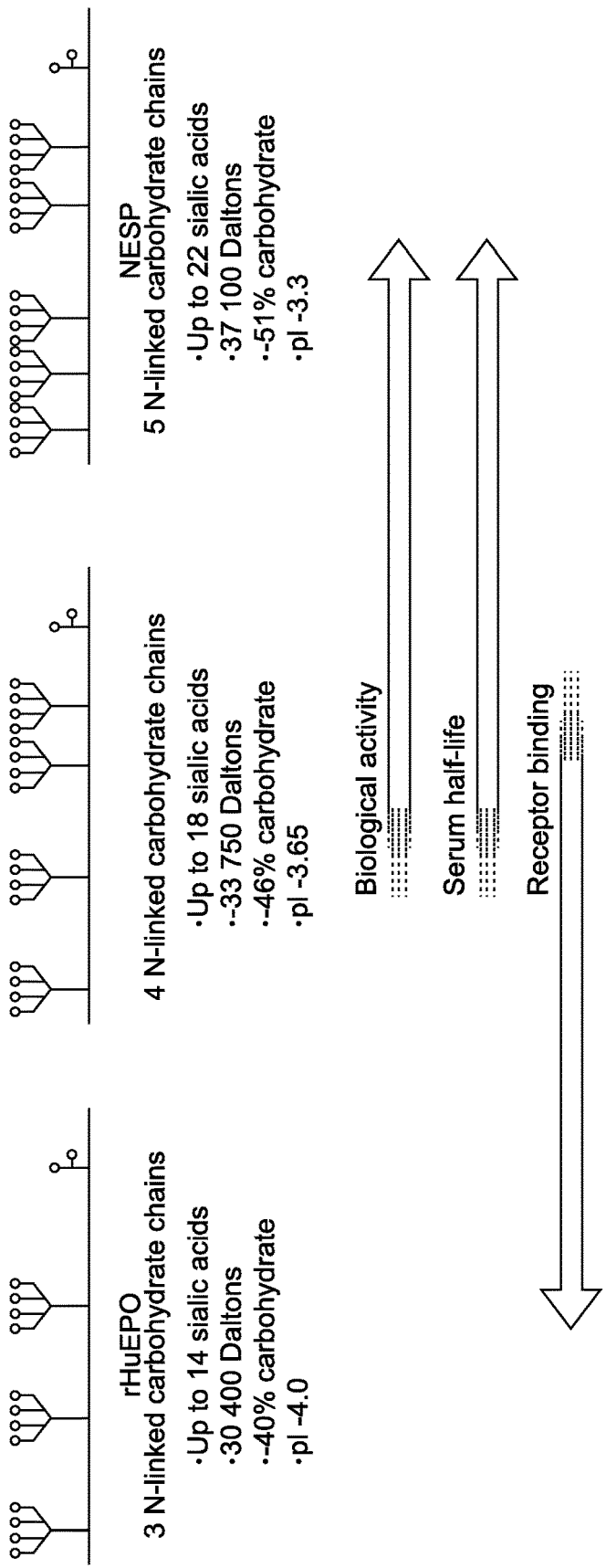
FIG. 1 shows biochemical and biological properties of recombinant modified EPO (rHuEPO) containing four and five N-linked carbohydrate chains.

Disclosed herein are EpoR protein agonists which are modified non-human mammalian EPOs comprising a non-human mammalian erythropoietin sequence having at least one added and/or at least one relocated glycosylation site. The disclosed EpoR protein agonists have reduced probability for inducing red cell aplasia and having a longer half-lives in serum, which allow for weekly dosing. Such, EpoR protein agonists initiate, facilitate or enhance a biological activity. For example, an EpoR protein agonist can be a biologically active ligand which binds to its complementary biologically active receptor and activates the latter either to cause a biological response in the receptor, or to enhance preexisting biological activity of the receptor.

Non-regenerative anemia (NRA) refers to a decrease in erythrocyte production. Anemia, the condition of having lower than normal numbers of red blood cells called erythrocytes, can have many clinical manifestations. Affected animals often suffer from decreased energy levels, pale or yellowed gums, an increased heart rate, and an intolerance to exercise. NRA in cats may be caused by chronic kidney diseases, feline leukemia virus, feline immunodeficiency virus, and cancer.

Pure red cell aplasia (PRCA or RCA) or erythroblastopenia refers to a type of anemia affecting the precursors to red blood cells but not to white blood cells. In PRCA, the bone marrow ceases to produce red blood cells. In cats, prior treatment with, for example, recombinant human EPO may lead to generation of antibodies against both the external human EPO and endogenous feline EPO, which can result in RCA in cats.

An EpoR protein agonist disclosed herein is a modified non-human mammalian erythropoietin having at least one additional site for glycosylation, and/or at least one relocation of at least one site for glycosylation. The added sites for glycosylation may result in a greater number of carbohydrate chains, and higher sialic acid content, than the native erythropoietin. Modified non-human mammalian erythropoietin comprising amino acid sequences which include the rearrangement of at least one site for glycosylation are also provided. Modified non-human mammalian erythropoietin comprising an addition of one or more amino acids to the carboxy terminal end of erythropoietin wherein the addition provides at least one glycosylation site are also included.

The present specification encompasses modified non-human mammalian EPO. A modified non-human erythropoietin is one having sufficient homology to a native mammalian EPO or a fragment of a native mammalian EPO such that the modified EPO has agonist activity for the mammalian EpoR. In one aspect, the modified EPO has a non-naturally occurring amino acid sequence and/or a non-naturally occurring glycosylation pattern. The mammalian EPO may be from a mammal, including feline, canine, mouse, rat, hamster, rabbit, guinea pig, ruminant, ferret, non-human primate, pig, Siberian tiger, giant panda, or pacific walrus.

The modifications described herein may be based on sequence differences at the nucleotide or amino acid level. A modified nucleic acid and/or amino acid sequence is a sequence that is different from the native sequence due to a deletion, an insertion, a non-conservative or conservative substitution or combinations thereof of one or more amino acid residues. In one embodiment, the modification is a point mutation. The modifications herein may also include the addition of glycosylation not occurring in the native host organism, a truncated protein (i.e., a protein fragment) and/or binding to or otherwise attaching to additional amino acids, nucleotide(s) or nucleotide sequences, aptamers, labels, drugs, antibodies, etc.

In one embodiment, a modified non-human mammalian erythropoietin disclosed herein may have 1-17 amino acid additions, deletions, or substitutions. In one aspect, the modified non-human mammalian erythropoietin has at least 1, at least 2, at least 3, at least 4, at least 5, at least 6, at least 7, at least 8, at least 9, at least 10, at least 11, at least 12, at least 13, at least 14, at least 15, at least 16, at least 17 amino acid additions, substitutions, or deletions. Substitutions may be conservative or non-conservative. In another aspect, the modified non-human mammalian erythropoietin may have at most 17, at most 16, at most 15, at most 14, at most 13, at most 12, at most 11, at most 10, at most 9, at most 10, at most 11, at most 12, at most 13, at most 14, at most 15, at most 16, or at most 17 amino acid additions, substitutions, or deletions. In yet another aspect, the modified non-human mammalian erythropoietin may have 1-17, 1-16, 1-15, 1-14, 1-13, 1-12, 1-10, 1-9, 1-8, 1-7, 1-6, 1-5, 1-4, 1-3, 1-2, 2-17, 2-16, 2-15, 2-4, 2-13, 2-12, 2-10, 2-9, 2-8, 2-7, 2-6, 2-5, 2-4, 2-3, 3-17, 3-16, 3-15, 3-4, 3-13, 3-12, 3-10, 3-9, 3-8, 3-7, 3-6, 3-5, 3-4, 4-17, 4-16, 4-15, 4-14, 4-13, 4-12, 4-10, 4-9, 4-8, 4-7, 4-6, 4-5, 5-17, 5-16, 5-15, 5-14, 5-13, 5-12, 5-10, 5-9, 5-8, 5-7, 5-6, 5-5, 6-17, 6-16, 6-15, 6-14, 6-13, 6-12, 6-10, 6-9, 6-8, 6-7, 7-17, 7-16, 7-15, 7-14, 7-13, 7-12, 7-10, 7-9, 7-8, 8-17, 8-16, 8-15, 8-14, 8-13, 8-12, 8-10, 8-9, 9-17, 9-16, 9-15, 9-14, 9-13, 9-12, 9-10, 10-17, 10-16, 10-15, 10-14, 10-13, 10-12, 11-17, 11-16, 11-15, 11-14, 11-13, 11-12, 12-17, 12-16, 12-15, 12-14, 12-13, 13-17, 13-16, 13-15, 13-14, 14-17, 14-16, 14-15, 15-17, 15-16, or 16-17 amino acid additions, substitutions or deletions. These additions, substitutions, or deletions may or may not add a glycosylation site.

In one embodiment, the present modified non-human mammalian EPO includes a set of substitutions denoted by the notation: Xaa$^{number}$, where Xaa is the three letter code for the amino acid to be substituted, and the number is the position into which the amino acid is substituted based on the sequence of the mammalian EPO. In aspects of this embodiment, the mammalian erythropoietin is feline erythropoietin where an asparagine residue is substituted for the amino acid residue at any one or more of positions 30, 51, 57, 69, 88, 89, 137, or 139. In other aspects of this embodiment, the mammalian erythropoietin is feline erythropoietin where either a serine or threonine residue is substituted for the amino acid residue at position 126.

In one embodiment, the mammalian erythropoietin is feline. In an aspect of this embodiment, a feline EPO is one having the sequence shown in SEQ ID NO: 5, wherein Xaa at position 18 is selected from E or G; and Xaa at position 116 is K or absent, a fragment thereof, or a variant thereof. In other aspects of this embodiment, a feline EPO disclosed herein may have, e.g., at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity with SEQ ID NO: 5, wherein Xaa at position 18 is selected from E or G; and Xaa at position 116 is K or absent. In yet other aspect of this embodiment, a feline EPO disclosed herein may have, e.g., at least 1, at least 2, at least 3, at least 4, at least 5, at least 6, at least 7, at least 8, at least 9, at least 10, at least 11, at least 12, at least 13, at least 14, at least 15, at least 16, at least 17 amino acid additions, substitutions, or deletions to SEQ ID NO: 5, wherein Xaa at position 18 is selected from E or G; and Xaa at position 116 is K or absent. In still other aspect of this embodiment, a feline EPO disclosed herein may have, e.g., at most 17, at most 16, at most 15, at most 14, at most 13, at most 12, at most 11, at most 10, at most 9, at most 10, at most 11, at most 12, at most 13, at most 14, at most 15, at most 16, or at most 17 amino acid additions, substitutions, or deletions to SEQ ID NO: 5, wherein Xaa at position 18 is selected from E or G; and Xaa at position 116 is K or absent. In other aspect of this embodiment, a feline EPO disclosed herein may have, e.g., 1-17, 1-16, 1-15, 1-14, 1-13, 1-12, 1-10, 1-9, 1-8, 1-7, 1-6, 1-5, 1-4, 1-3, 1-2, 2-17, 2-16, 2-15, 2-4, 2-13, 2-12, 2-10, 2-9, 2-8, 2-7, 2-6, 2-5, 2-4, 2-3, 3-17, 3-16, 3-15, 3-4, 3-13, 3-12, 3-10, 3-9, 3-8, 3-7, 3-6, 3-5, 3-4, 4-17, 4-16, 4-15, 4-14, 4-13, 4-12, 4-10, 4-9, 4-8, 4-7, 4-6, 4-5, 5-17, 5-16, 5-15, 5-14, 5-13, 5-12, 5-10, 5-9, 5-8, 5-7, 5-6, 5-5, 6-17, 6-16, 6-15, 6-14, 6-13, 6-12, 6-10, 6-9, 6-8, 6-7, 7-17, 7-16, 7-15, 7-14, 7-13, 7-12, 7-10, 7-9, 7-8, 8-17, 8-16, 8-15, 8-14, 8-13, 8-12, 8-10, 8-9, 9-17, 9-16, 9-15, 9-14, 9-13, 9-12, 9-10, 10-17, 10-16, 10-15, 10-14, 10-13, 10-12, 11-17, 11-16, 11-15, 11-14, 11-13, 11-12, 12-17, 12-16, 12-15, 12-14, 12-13, 13-17, 13-16, 13-15, 13-14, 14-17, 14-16, 14-15, 15-17, 15-16, or 16-17 amino acid additions, substitutions or deletions to SEQ ID NO: 5, wherein Xaa at position 18 is selected from E or G; and Xaa at position 116 is K or absent. These additions, substitutions, or deletions may or may not add a glycosylation site. Substitutions may be conservative or non-conservative.

In an aspect of this embodiment, a feline EPO is one having the sequence shown in SEQ ID NO: 6, wherein Xaa at position 18 is selected from E or G; and Xaa at position 116 is K or absent, a fragment thereof, or a variant thereof. In other aspects of this embodiment, a feline EPO disclosed herein is one having, e.g., at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity with SEQ ID NO: 6, wherein Xaa at position 18 is selected from E or G; and Xaa at position 116 is K or absent. In yet other aspect of this embodiment, a feline EPO disclosed herein may have, e.g., at least 1, at least 2, at least 3, at least 4, at least 5, at least 6, at least 7, at least 8, at least 9, at least 10, at least 11, at least 12, at least 13, at least 14, at least 15, at least 16, at least 17 amino acid additions, substitutions, or deletions to SEQ ID NO: 6, wherein Xaa at position 18 is selected from E or G; and Xaa at position 116 is K or absent. In still other aspect of this embodiment, a feline EPO disclosed herein may have, e.g., at most 17, at most 16, at most 15, at most 14, at most 13, at most 12, at most 11, at most 10, at most 9, at most 10, at most 11, at most 12, at most 13, at most 14, at most 15, at most 16, or at most 17 amino acid additions, substitutions, or deletions to SEQ ID NO: 6, wherein Xaa at position 18 is selected from E or G; and Xaa at position 116 is K or absent. In other aspect of this embodiment, a feline EPO disclosed herein may have, e.g., 1-17, 1-16, 1-15, 1-14, 1-13, 1-12, 1-10, 1-9, 1-8, 1-7, 1-6, 1-5, 1-4, 1-3, 1-2, 2-17, 2-16, 2-15, 2-4, 2-13, 2-12, 2-10, 2-9, 2-8, 2-7, 2-6, 2-5, 2-4, 2-3, 3-17, 3-16, 3-15, 3-4, 3-13, 3-12, 3-10, 3-9, 3-8, 3-7, 3-6, 3-5, 3-4, 4-17, 4-16, 4-15, 4-14, 4-13, 4-12, 4-10, 4-9, 4-8, 4-7, 4-6, 4-5, 5-17, 5-16, 5-15, 5-14, 5-13, 5-12, 5-10, 5-9, 5-8, 5-7, 5-6, 5-5, 6-17, 6-16, 6-15, 6-14, 6-13, 6-12, 6-10, 6-9, 6-8, 6-7, 7-17, 7-16, 7-15, 7-14, 7-13, 7-12, 7-10, 7-9, 7-8, 8-17, 8-16, 8-15, 8-14, 8-13, 8-12, 8-10, 8-9, 9-17, 9-16, 9-15, 9-14, 9-13, 9-12, 9-10, 10-17, 10-16, 10-15, 10-14, 10-13, 10-12, 11-17, 11-16, 11-15, 11-14, 11-13, 11-12, 12-17, 12-16, 12-15, 12-14, 12-13, 13-17, 13-16, 13-15, 13-14, 14-17, 14-16, 14-15, 15-17, 15-16, or 16-17 amino acid additions, substitutions or deletions to SEQ ID NO: 6, wherein Xaa at position 18 is selected from E or G; and Xaa at position 116 is K or absent. These additions, substitutions, or deletions may or may not add a glycosylation site. Substitutions may be conservative or non-conservative.

In another embodiment, the modified mammalian erythropoietin is canine. In an aspect of this embodiment, a canine EPO is one having the sequence shown in SEQ ID NO: 10, a fragment thereof, or a variant thereof. In aspects of this embodiment, a modified canine EPO disclosed herein may have, e.g., at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity with SEQ ID NO: 10. In yet other aspect of this embodiment, a modified canine EPO disclosed herein may have, e.g., at least 1, at least 2, at least 3, at least 4, at least 5, at least 6, at least 7, at least 8, at least 9, at least 10, at least 11, at least 12, at least 13, at least 14, at least 15, at least 16, at least 17 amino acid additions, substitutions, or deletions to SEQ ID NO: 10. In still other aspect of this embodiment, a modified canine EPO disclosed herein may have, e.g., at most 17, at most 16, at most 15, at most 14, at most 13, at most 12, at most 11, at most 10, at most 9, at most 10, at most 11, at most 12, at most 13, at most 14, at most 15, at most 16, or at most 17 amino acid additions, substitutions, or deletions to SEQ ID NO: 10. In other aspect of this embodiment, a modified canine EPO disclosed herein may have, e.g., 1-17, 1-16, 1-15, 1-14, 1-13, 1-12, 1-10, 1-9, 1-8, 1-7, 1-6, 1-5, 1-4, 1-3, 1-2, 2-17, 2-16, 2-15, 2-4, 2-13, 2-12, 2-10, 2-9, 2-8, 2-7, 2-6, 2-5, 2-4, 2-3, 3-17, 3-16, 3-15, 3-4, 3-13, 3-12, 3-10, 3-9, 3-8, 3-7, 3-6, 3-5, 3-4, 4-17, 4-16, 4-15, 4-14, 4-13, 4-12, 4-10, 4-9, 4-8, 4-7, 4-6, 4-5, 5-17, 5-16, 5-15, 5-14, 5-13, 5-12, 5-10, 5-9, 5-8, 5-7, 5-6, 5-5, 6-17, 6-16, 6-15, 6-14, 6-13, 6-12, 6-10, 6-9, 6-8, 6-7, 7-17, 7-16, 7-15, 7-14, 7-13, 7-12, 7-10, 7-9, 7-8, 8-17, 8-16, 8-15, 8-14, 8-13, 8-12, 8-10, 8-9, 9-17, 9-16, 9-15, 9-14, 9-13, 9-12, 9-10, 10-17, 10-16, 10-15, 10-14, 10-13, 10-12, 11-17, 11-16, 11-15, 11-14, 11-13, 11-12, 12-17, 12-16, 12-15, 12-14, 12-13, 13-17, 13-16, 13-15, 13-14, 14-17, 14-16, 14-15, 15-17, 15-16, or 16-17 amino acid additions, substitutions or deletions to SEQ ID NO: 10. These additions, substitutions, or deletions may or may not add a glycosylation site. Substitutions may be conservative or non-conservative.

In another embodiment, a modified mammalian erythropoietin is canine. In an aspect of this embodiment, a modified canine EPO is one having the sequence shown in SEQ ID NO: 11, a fragment thereof, or a variant thereof. In aspects of this embodiment, a modified canine EPO disclosed herein may have, e.g., at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity with SEQ ID NO: 11. In yet other aspect of this embodiment, a modified canine EPO disclosed herein may have, e.g., at least 1, at least 2, at least 3, at least 4, at least 5, at least 6, at least 7, at least 8, at least 9, at least 10, at least 11, at least 12, at least 13, at least 14, at least 15, at least 16, at least 17 amino acid additions, substitutions, or deletions to SEQ ID NO: 11. In still other aspect of this embodiment, a modified canine EPO disclosed herein may have, e.g., at most 17, at most 16, at most 15, at most 14, at most 13, at most 12, at most 11, at most 10, at most 9, at most 10, at most 11, at most 12, at most 13, at most 14, at most 15, at most 16, or at most 17 amino acid additions, substitutions, or deletions to SEQ ID NO: 11. In other aspect of this embodiment, a canine EPO disclosed herein may have, e.g., 1-17, 1-16, 1-15, 1-14, 1-13, 1-12, 1-10, 1-9, 1-8, 1-7, 1-6, 1-5, 1-4, 1-3, 1-2, 2-17, 2-16, 2-15, 2-4, 2-13, 2-12, 2-10, 2-9, 2-8, 2-7, 2-6, 2-5, 2-4, 2-3, 3-17, 3-16, 3-15, 3-4, 3-13, 3-12, 3-10, 3-9, 3-8, 3-7, 3-6, 3-5, 3-4, 4-17, 4-16, 4-15, 4-14, 4-13, 4-12, 4-10, 4-9, 4-8, 4-7, 4-6, 4-5, 5-17, 5-16, 5-15, 5-14, 5-13, 5-12, 5-10, 5-9, 5-8, 5-7, 5-6, 5-5, 6-17, 6-16, 6-15, 6-14, 6-13, 6-12, 6-10, 6-9, 6-8, 6-7, 7-17, 7-16, 7-15, 7-14, 7-13, 7-12, 7-10, 7-9, 7-8, 8-17, 8-16, 8-15, 8-14, 8-13, 8-12, 8-10, 8-9, 9-17, 9-16, 9-15, 9-14, 9-13, 9-12, 9-10, 10-17, 10-16, 10-15, 10-14, 10-13, 10-12, 11-17, 11-16, 11-15, 11-14, 11-13, 11-12, 12-17, 12-16, 12-15, 12-14, 12-13, 13-17, 13-16, 13-15, 13-14, 14-17, 14-16, 14-15, 15-17, 15-16, or 16-17 amino acid additions, substitutions or deletions to SEQ ID NO: 11. These additions, substitutions, or deletions may or may not add a glycosylation site. Substitutions may be conservative or non-conservative.

A modified non-human mammalian erythropoietin disclosed herein may be glycosylated or unglycosylated. That is, one or more sugar residues or carbohydrate chains may be attached to the glycosylation sites of the modified non-human mammalian erythropoietin. This glycosylation can be performed by enzymatic glycosylation during or after translation and assembly of the modified non-human mammalian erythropoietin. Typically the structure of the glycosylation site is directed to the attachment of a carbohydrate residue or polymer. The "polymer" is a molecule formed by covalent linkage of two or more monomers, wherein none of the monomers is an amino acid residue. The term is intended to cover carbohydrate molecules or chains attached by in vitro glycosylation, i.e., a synthetic glycosylation performed in vitro normally involving covalently linking a carbohydrate molecule to an attachment group of the polypeptide, optionally using a cross-linking agent.

In one embodiment the attachment of the carbohydrate is either O-linked or N-linked. O-linked glycosidic typically attach at specific amino acid residues, such as serine, threonine, hydroxyproline, or hydroxylysine. In one embodiment, the addition of or relocation of a serine or threonine may add a glycosylation site to the mammalian erythropoietin. N-linked glycosidic chains typically attach at specific amino acid sequences, such as Asn-Xaa-Ser/Thr/Cystein. Xaa as used in this context may be any amino acid.

A modified non-human mammalian EPO disclosed herein includes at least one additional and/or at least one relocated glycosylation site. In one embodiment, a glycosylation site is added to a mammalian erythropoietin, resulting in a modified non-human mammalian erythropoietin disclosed herein. This addition may be completed by adding amino acid residue(s) to either end of the mammalian erythropoietin, by adding amino acid residue(s) between internal amino acids of the mammalian erythropoietin or by replacing one or more amino acid residues in the mammalian erythropoietin with the amino acid(s) which may attach a glycosidic chain.

In one embodiment, a glycosylation site is relocated within a mammalian erythropoietin, resulting in a modified non-human mammalian erythropoietin disclosed herein. That is, the amino acid(s) of a glycosylation site in the native protein are replaced with amino acids which cannot be glycosylated with carbohydrate chains, and a glycosylation site is added elsewhere to obtain a modified non-human mammalian erythropoietin sequence.

In an embodiment, a feline EpoR protein agonist is modified feline EPO, which include at least one additional site for glycosylation, and/or a relocation of at least one site for glycosylation. In aspects of this embodiment, an EpoR protein agonist is a feline EPO or a modified feline EPO disclosed herein having one of the following sets of substituted amino acids: Asn$^{30}$Thr$^{32}$ EPO; Asn$^{51}$Thr$^{53}$ EPO; Asn$^{57}$Thr$^{59}$ EPO; Asn$^{69}$EPO; Asn$^{69}$Thr$^{71}$ EPO; Ser$^{68}$Asn$^{69}$Thr$^{71}$ EPO; Val$^{87}$Asn$^{88}$ EPO; Ser$^{87}$Asn$^{88}$ EPO; ser$^{87}$Asn$^{88}$G EPO; Ser$^{87}$Asn$^{88}$Thr$^{92}$ EPO; Ser$^{87}$Asn$^{88}$Ala$^{163}$ EPO; Asn$^{69}$Thr$^{71}$Ser$^{87}$Ase EPO; Asn$^{30}$Thr$^{32}$ Val$^{87}$Asn$^{88}$ EPO; Asn$^{89}$Ile$^{90}$Thr$^{91}$ EPO; Ser$^{87}$Asn$^{89}$Ile$^{90}$Thr$^{91}$ EPO; Asn$^{137}$Thr$^{139}$ EPO; Asn$^{139}$Thr$^{141}$ EPO; Thr$^{126}$ EPO; or Pro$^{125}$Thr$^{126}$ EPO. In other aspects of this embodiment, an EpoR protein agonist is a feline EPO or a modified feline EPO disclosed herein having one or more of the following substitution sets is present: Ser$^{87}$Asn$^{88}$ and/or Asn$^{30}$Thr$^{32}$Val$^{87}$Asn$^{88}$.

In aspects of this embodiment, an EpoR protein agonist is a feline EPO of SEQ ID NO: 5, wherein Xaa at position 18 is selected from E or G; and Xaa at position 116 is K or absent, having one of the following sets of substituted amino acids: Asn$^{30}$Thr$^{32}$ EPO; Asn$^{51}$Thr$^{53}$ EPO; Asn$^{57}$Thr$^{59}$ EPO; Asn$^{69}$EPO; Asn$^{69}$Thr$^{71}$ EPO; Ser$^{68}$Asn$^{69}$Thr$^{71}$ EPO; Val$^{87}$Asn$^{88}$ EPO; Ser$^{87}$Asn$^{88}$ EPO; Ser$^{87}$Asn$^{88}$Gly$^{89}$ EPO; Ser$^{87}$Asn$^{88}$Thr$^{92}$ EPO; Ser$^{87}$Asn$^{88}$Ala$^{163}$ EPO; Asn$^{69}$Thr$^{71}$Ser$^{87}$Asn$^{88}$ EPO; Asn$^{30}$Thr$^{32}$Val$^{87}$Asn$^{88}$ EPO; Asn$^{89}$Ile$^{90}$Thr$^{91}$ EPO; Ser$^{87}$Asn$^{89}$Ile$^{90}$Thr$^{91}$ EPO; Asn$^{137}$Thr$^{139}$ EPO; Asn$^{139}$Thr$^{141}$ EPO; Thr$^{126}$ EPO; or Pro$^{125}$Thr$^{126}$ EPO. In other aspects of this embodiment, an EpoR protein agonist is a feline EPO of SEQ ID NO: 5, wherein Xaa at position 18 is selected from E or G; and Xaa at position 116 is K or absent, having one or more of the following substitution sets is present: Ser$^{87}$Asn$^{88}$ and/or Asn$^{30}$Thr$^{32}$Val$^{87}$Asn$^{88}$.

In one embodiment the mammalian erythropoietin is a feline EPO or a modified feline EPO disclosed herein modified by deleting one or more of the glycosylation sites that attach to N-linked carbohydrate chains and by adding a glycosylation site that attaches to an N-linked carbohydrate chain at amino acid position 88. In one aspect of this embodiment, one of the following amino acid substitution sets is present: Gln$^{24}$Ser$^{87}$Asn$^{88}$; Gln$^{38}$Ser$^{87}$Asn$^{88}$; or Gln$^{83}$Ser$^{87}$Asn$^{88}$.

In a further embodiment, an EpoR protein agonist has an amino acid sequence of SEQ ID No. 6, whereas Xaa at position 18 is selected from E or G; and Xaa at position 116 is K or absent. In aspects of this embodiment, an EpoR protein agonist has at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity with SEQ ID NO: 6, whereas Xaa at position 18 is selected from E or G; and Xaa at position 116 is K or absent.

Additional sequences may also be added to the mammalian erythropoietin to obtain a modified non-human mammalian EPO. For instance, in one embodiment, the glycosylation sequence comprises a fragment of a mammalian chorionic gonadotropin or a sequence having at least 70% sequence homology thereto. In one aspect, fragment of mammalian chorionic gonadotropin is a fragment from the carboxy terminal (aka "C-terminal") region of the mammalian chorionic gonadotropin or a sequence having at least 70% sequence homology thereto. In one aspect, the carboxy terminal of the mammalian chorionic gonadotropin comprises at least 50% of the protein located at the C terminal. In one embodiment, the carboxy terminal of the mammalian chorionic gonadotropin includes at least 40% of the protein from the C-terminal, at least 30% of the protein from the C-terminal, at least 25% of the protein from the C-terminal, at least 20% of the protein from the C-terminal, or at least 10% of the protein from the C-terminal.

Optionally, a mammalian EPO disclosed herein includes a signal sequence. In an aspect of this embodiment, a signal sequence disclosed herein includes a signal sequence from human EPO (SEQ ID NO: 9), a signal sequence from feline EPO (SEQ ID NO: 12), or a signal sequence from canine EPO (SEQ ID NO: 13) or another conventionally recognized signal sequence. For instance, SEQ ID NO 11 is a canine EPO including a signal sequence (amino acids 1-26).

In one embodiment, the chorionic gonadotropin is human chorionic gonadotropin. In an aspect of this embodiment, a chorionic gonadotrophin comprises SEQ ID NO: 8, or a sequence having, e.g., at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity with SEQ ID NO: 8. In an aspect of this embodiment, a chorionic gonadotrophin comprises an amino acid sequence having 1, 2, 3, 4, 5, 1-2, 1-3, 1-4, 1-5, 2-3, 2-4, 2-5, 3-4, 3-5, or 4-5 amino acid additions, deletions or substitutions to SEQ ID NO: 8.

The present specification also discloses nucleic acid sequences encoding modified non-human mammalian EPO disclosed herein. The nucleic acid sequence may include introns or may be a cDNA. The nucleic acid sequence may also encode a sequence which is cleaved off after translation. The nucleic acids may be DNA or RNA. The nucleic acids described herein may also include the complements of the coding sequences.

The present specification also discloses a fusion protein, comprising a peptide, a linker and a Fc fragment, wherein the peptide is fused through linker to the Fc fragment. A peptide disclosed herein may be one with the amino acid sequence of SEQ ID NO: 1 wherein Xaa at position 13 is Trp, 1-naphthylalanine, or 2-naphthylalanine, or a sequence having, e.g., at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity to the amino acid sequence of SEQ ID NO: 1 wherein Xaa at position 13 is Trp, 1-naphthylalanine, or 2-naphthylalanine. In an aspect of this embodiment, a peptide disclosed herein comprises an amino acid sequence having 1, 2, 3, 4, 5, 1-2, 1-3, 1-4, 1-5, 2-3, 2-4, 2-5, 3-4, 3-5, or 4-5 amino acid additions, deletions or substitutions to SEQ ID NO: 1 wherein Xaa at position 13 is Trp, 1-naphthylalanine, or 2-naphthylalanine.

A peptide disclosed herein may be a feline EPO as disclosed herein. In aspects of this embodiment, a feline EPO disclosed herein may be SEQ ID NO: 5, wherein Xaa at position 18 is selected from E or G; and Xaa at position 116 is K or absent, or a sequence having, e.g., at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity to the amino acid sequence of SEQ ID NO: 5, wherein Xaa at position 18 is selected from E or G; and Xaa at position 116 is K or absent. In other aspect of this embodiment, a feline EPO disclosed herein is one having, e.g., at least 1, at least 2, at least 3, at least 4, at least 5, at least 6, at least 7, at least 8, at least 9, at least 10, at least 11, at least 12, at least 13, at least 14, at least 15, at least 16, at least 17 amino acid additions, substitutions, or deletions to SEQ ID NO: 5, wherein Xaa at position 18 is selected from E or G; and Xaa at position 116 is K or absent. In yet other aspect of this embodiment, a feline EPO disclosed herein may have, e.g., at most 17, at most 16, at most 15, at most 14, at most 13, at most 12, at most 11, at most 10, at most 9, at most 10, at most 11, at most 12, at most 13, at most 14, at most 15, at most 16, or at most 17 amino acid additions, substitutions, or deletions to SEQ ID NO: 5, wherein Xaa at position 18 is selected from E or G; and Xaa at position 116 is K or absent. In still other aspect of this embodiment, a feline EPO disclosed herein may have, e.g., 1-17, 1-16, 1-15, 1-14, 1-13, 1-12, 1-10, 1-9, 1-8, 1-7, 1-6, 1-5, 1-4, 1-3, 1-2, 2-17, 2-16, 2-15, 2-4, 2-13, 2-12, 2-10, 2-9, 2-8, 2-7, 2-6, 2-5, 2-4, 2-3, 3-17, 3-16, 3-15, 3-4, 3-13, 3-12, 3-10, 3-9, 3-8, 3-7, 3-6, 3-5, 3-4, 4-17, 4-16, 4-15, 4-14, 4-13, 4-12, 4-10, 4-9, 4-8, 4-7, 4-6, 4-5, 5-17, 5-16, 5-15, 5-14, 5-13, 5-12, 5-10, 5-9, 5-8, 5-7, 5-6, 5-5, 6-17, 6-16, 6-15, 6-14, 6-13, 6-12, 6-10, 6-9, 6-8, 6-7, 7-17, 7-16, 7-15, 7-14, 7-13, 7-12, 7-10, 7-9, 7-8, 8-17, 8-16, 8-15, 8-14, 8-13, 8-12, 8-10, 8-9, 9-17, 9-16, 9-15, 9-14, 9-13, 9-12, 9-10, 10-17, 10-16, 10-15, 10-14, 10-13, 10-12, 11-17, 11-16, 11-15, 11-14, 11-13, 11-12, 12-17, 12-16, 12-15, 12-14, 12-13, 13-17, 13-16, 13-15, 13-14, 14-17, 14-16, 14-15, 15-17, 15-16, or 16-17 amino acid additions, substitutions or deletions to SEQ ID NO: 5, wherein Xaa at position 18 is selected from E or G; and Xaa at position 116 is K or absent. These additions, substitutions, or deletions may or may not add a glycosylation site. Substitutions may be conservative or non-conservative.

A peptide disclosed herein may be a modified feline EPO. A modified feline EPO disclosed herein may be SEQ ID NO: 6, or a sequence having, e.g., at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity to the amino acid sequence of SEQ ID NO: 6. In other aspect of this embodiment, a modified feline EPO disclosed herein may have, e.g., at least 1, at least 2, at least 3, at least 4, at least 5, at least 6, at least 7, at least 8, at least 9, at least 10, at least 11, at least 12, at least 13, at least 14, at least 15, at least 16, at least 17 amino acid additions, substitutions, or deletions to SEQ ID NO: 6. In yet other aspect of this embodiment, a modified feline EPO disclosed herein may have, e.g., at most 17, at most 16, at most 15, at most 14, at most 13, at most 12, at most 11, at most 10, at most 9, at most 10, at most 11, at most 12, at most 13, at most 14, at most 15, at most 16, or at most 17 amino acid additions, substitutions, or deletions to SEQ ID NO: 6. In still other aspect of this embodiment, a modified feline EPO disclosed herein may have, e.g., 1-17, 1-16, 1-15, 1-14, 1-13, 1-12, 1-10, 1-9, 1-8, 1-7, 1-6, 1-5, 1-4, 1-3, 1-2, 2-17, 2-16, 2-15, 2-4, 2-13, 2-12, 2-10, 2-9, 2-8, 2-7, 2-6, 2-5, 2-4, 2-3, 3-17, 3-16, 3-15, 3-4, 3-13, 3-12, 3-10, 3-9, 3-8, 3-7, 3-6, 3-5, 3-4, 4-17, 4-16, 4-15, 4-14, 4-13, 4-12, 4-10, 4-9, 4-8, 4-7, 4-6, 4-5, 5-17, 5-16, 5-15, 5-14, 5-13, 5-12, 5-10, 5-9, 5-8, 5-7, 5-6, 5-5, 6-17, 6-16, 6-15, 6-14, 6-13, 6-12, 6-10, 6-9, 6-8, 6-7, 7-17, 7-16, 7-15, 7-14, 7-13, 7-12, 7-10, 7-9, 7-8, 8-17, 8-16, 8-15, 8-14, 8-13, 8-12, 8-10, 8-9, 9-17, 9-16, 9-15, 9-14, 9-13, 9-12, 9-10, 10-17, 10-16, 10-15, 10-14, 10-13, 10-12, 11-17, 11-16, 11-15, 11-14, 11-13, 11-12, 12-17, 12-16, 12-15, 12-14, 12-13, 13-17, 13-16, 13-15, 13-14, 14-17, 14-16, 14-15, 15-17, 15-16, or 16-17 amino acid additions, substitutions or deletions to SEQ ID NO: 6. These additions, substitutions, or deletions may or may not add a glycosylation site. Substitutions may be conservative or non-conservative.

A peptide disclosed herein may be a modified canine EPO. A canine EPO disclosed herein may be SEQ ID NO: 10, a fragment thereof, or a variant thereof. In aspects of this embodiment, a canine EPO disclosed herein may have, e.g., at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity with SEQ ID NO: 10. In yet other aspect of this embodiment, a canine EPO disclosed herein may have, e.g., at least 1, at least 2, at least 3, at least 4, at least 5, at least 6, at least 7, at least 8, at least 9, at least 10, at least 11, at least 12, at least 13, at least 14, at least 15, at least 16, at least 17 amino acid additions, substitutions, or deletions to SEQ ID NO: 10. In still other aspect of this embodiment, a canine EPO disclosed herein may have, e.g., at most 17, at most 16, at most 15, at most 14, at most 13, at most 12, at most 11, at most 10, at most 9, at most 10, at most 11, at most 12, at most 13, at most 14, at most 15, at most 16, or at most 17 amino acid additions, substitutions, or deletions to SEQ ID NO: 10. In other aspect of this embodiment, a canine EPO disclosed herein may have, e.g., 1-17, 1-16, 1-15, 1-14, 1-13, 1-12, 1-10, 1-9, 1-8, 1-7, 1-6, 1-5, 1-4, 1-3, 1-2, 2-17, 2-16, 2-15, 2-4, 2-13, 2-12, 2-10, 2-9, 2-8, 2-7, 2-6, 2-5, 2-4, 2-3, 3-17, 3-16, 3-15, 3-4, 3-13, 3-12, 3-10, 3-9, 3-8, 3-7, 3-6, 3-5, 3-4, 4-17, 4-16, 4-15, 4-14, 4-13, 4-12, 4-10, 4-9, 4-8, 4-7, 4-6, 4-5, 5-17, 5-16, 5-15, 5-14, 5-13, 5-12, 5-10, 5-9, 5-8, 5-7, 5-6, 5-5, 6-17, 6-16, 6-15, 6-14, 6-13, 6-12, 6-10, 6-9, 6-8, 6-7, 7-17, 7-16, 7-15, 7-14, 7-13, 7-12, 7-10, 7-9, 7-8, 8-17, 8-16, 8-15, 8-14, 8-13, 8-12, 8-10, 8-9, 9-17, 9-16, 9-15, 9-14, 9-13, 9-12, 9-10, 10-17, 10-16, 10-15, 10-14, 10-13, 10-12, 11-17, 11-16, 11-15, 11-14, 11-13, 11-12, 12-17, 12-16, 12-15, 12-14, 12-13, 13-17, 13-16, 13-15, 13-14, 14-17, 14-16, 14-15, 15-17, 15-16, or 16-17 amino acid additions, substitutions or deletions to SEQ ID NO: 10. These additions, substitutions, or deletions may or may not add a glycosylation site. Substitutions may be conservative or non-conservative.

A peptide disclosed herein may be a modified canine EPO. A canine EPO disclosed herein may be SEQ ID NO: 11, a fragment thereof, or a variant thereof. In aspects of this embodiment, a canine EPO disclosed herein may have, e.g., at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity with SEQ ID NO: 11. In yet other aspect of this embodiment, a canine EPO disclosed herein may have, e.g., at least 1, at least 2, at least 3, at least 4, at least 5, at least 6, at least 7, at least 8, at least 9, at least 10, at least 11, at least 12, at least 13, at least 14, at least 15, at least 16, at least 17 amino acid additions, substitutions, or deletions to SEQ ID NO: 11. In still other aspect of this embodiment, a canine EPO disclosed herein may have, e.g., at most 17, at most 16, at most 15, at most 14, at most 13, at most 12, at most 11, at most 10, at most 9, at most 10, at most 11, at most 12, at most 13, at most 14, at most 15, at most 16, or at most 17 amino acid additions, substitutions, or deletions to SEQ ID NO: 11. In other aspect of this embodiment, a canine EPO disclosed herein may have, e.g., 1-17, 1-16, 1-15, 1-14, 1-13, 1-12, 1-10, 1-9, 1-8, 1-7, 1-6, 1-5, 1-4, 1-3, 1-2, 2-17, 2-16, 2-15, 2-4, 2-13, 2-12, 2-10, 2-9, 2-8, 2-7, 2-6, 2-5, 2-4, 2-3, 3-17, 3-16, 3-15, 3-4, 3-13, 3-12, 3-10, 3-9, 3-8, 3-7, 3-6, 3-5, 3-4, 4-17, 4-16, 4-15, 4-14, 4-13, 4-12, 4-10, 4-9, 4-8, 4-7, 4-6, 4-5, 5-17, 5-16, 5-15, 5-14, 5-13, 5-12, 5-10, 5-9, 5-8, 5-7, 5-6, 5-5, 6-17, 6-16, 6-15, 6-14, 6-13, 6-12, 6-10, 6-9, 6-8, 6-7, 7-17, 7-16, 7-15, 7-14, 7-13, 7-12, 7-10, 7-9, 7-8, 8-17, 8-16, 8-15, 8-14, 8-13, 8-12, 8-10, 8-9, 9-17, 9-16, 9-15, 9-14, 9-13, 9-12, 9-10, 10-17, 10-16, 10-15, 10-14, 10-13, 10-12, 11-17, 11-16, 11-15, 11-14, 11-13, 11-12, 12-17, 12-16, 12-15, 12-14, 12-13, 13-17, 13-16, 13-15, 13-14, 14-17, 14-16, 14-15, 15-17, 15-16, or 16-17 amino acid additions, substitutions or deletions to SEQ ID NO: 11. These additions, substitutions, or deletions may or may not add a glycosylation site. Substitutions may be conservative or non-conservative.

In one embodiment, a peptides disclosed herein is selected from the amino acid sequences disclosed in U.S. Pat. No. 6,703,480, the entire contents of which are hereby expressly incorporated by reference. In one embodiment, a peptide disclosed herein is SEQ ID NO: 1, wherein Xaa at position 13 is Trp, 1-naphthylalanine, or 2-naphthylalanine.

The term "Fc fragment" or "immunoglobulin Fc region" as used herein, refers to a protein that contains the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region. Also, the immunoglobulin Fc region disclosed herein may contain a part or all of the Fc region including the heavy-chain constant region 1 (CH1) and/or the light-chain constant region 1 (CL1), except for the variable regions of the heavy and light chains, as long as it has a physiological function substantially similar to or better than the native protein. Also, the immunoglobulin Fc region may be a fragment having a deletion in a relatively long portion of the amino acid sequence of CH2 and/or CH3. That is, the immunoglobulin Fc region disclosed herein may comprise 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

The immunoglobulin Fc region disclosed herein includes a native amino acid sequence, and a modified sequence (mutant) thereof. A modified amino acid sequence is a sequence that is different from the native amino acid sequence due to a deletion, an insertion, a non-conservative or conservative substitution or combinations thereof of one or more amino acid residues.

Also, other variants of the Fc are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site and an ADCC (antibody dependent cell mediated cytotoxicity) site. Techniques of preparing such sequence variants of the immunoglobulin Fc region are disclosed in WO 97/34631 and WO 96/32478.

The aforementioned Fc variants are variants that have a biological activity identical to the Fc region disclosed herein or improved structural stability, for example, against heat, pH, or the like.

In addition, these Fc regions may be obtained from native forms isolated from cats and other animals including dogs, cows, goats, pigs, mice, rabbits, hamsters, rats and guinea pigs, or may be recombinants, variants, or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)2 fragments. These fragments may be subjected, for example, to size exclusion chromatography to isolate Fc or pF'c. Preferably, a feline-derived Fc region is a recombinant immunoglobulin Fc region that is obtained from a microorganism.

In addition, the immunoglobulin Fc region disclosed herein may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. The removal of sugar chains from an Fc region results in a sharp decrease in binding affinity to the C1q part of the first complement component C1 and a decrease or loss in antibody-dependent cell-mediated cytotoxicity or complement-dependent cytotoxicity, thereby not inducing unnecessary immune responses in vivo. In this regard, an immunoglobulin Fc region in a deglycosylated or aglycosylated form may be more suitable to the object disclosed herein as a drug carrier.

As used herein, the term "deglycosylation" refers to enzymatically removing sugar moieties from an Fc region, and the term "aglycosylation" means that an Fc region is produced in an unglycosylated form by a prokaryote, preferably *E. coli*.

In addition, the immunoglobulin Fc region may be an Fc region that is derived from a IgG, IgA, IgD, IgE and IgM, or that is made by combinations thereof or hybrids thereof. In one embodiment it is derived from a mammalian IgG or IgM, which are among the most abundant proteins in human blood, and most preferably from IgG, which is known to enhance the half-lives of ligand-binding proteins. In one embodiment, the immunoglobulin Fc region is an Fc region derived from feline IgG, IgA, IgE, or IgM.

On the other hand, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

Meanwhile, the Fc fragment or the Fc region of the dummy antibody may be modified to increase its affinity with neonatal Fc receptor (FcRN) and further extend its half-life in vivo. As mentioned above, Fc may be used as carrier to extend the in vivo half-lives of therapeutic peptides. Fc fusion proteins have in vivo half-lives ranging from a few days to over a week. Meanwhile, a full antibody molecule may also be used as carrier for therapeutic peptides. Antibody molecules can have in vivo half-lives over 3 weeks.

In addition, modifications can be made to the Fc domain to further extend the in vivo half-life of an antibody molecule or an Fc fusion protein. For example, introduction of mutations T250Q/M428L to an IgG1 molecule led to a significant increase in the serum half-life of the IgG1 molecule, also as disclosed in U.S. Pat. No. 7,217,798. Other mutations have also been made to increase the binding affinity of Fc to FcRN and extend the serum half-life, such as disclosed in U.S. Pat. No. 8,394,925.

Another modification, referred as "knob-and-hole" may also be made to the Fc region to form heterogeneous dimers. Antibody molecules have heavy chains and light chains. It is convenient to fuse two different peptides to an antibody molecule. Fc fusion proteins are often homo-dimers. However, hetero-dimers can also be constructed. For example, U.S. Pat. No. 7,642,228 disclosed that heterodimers of antibodies and Fc-fusion proteins can be constructed using the Knob-and-Hole concept.

A Fc fragment disclosed herein may be a feline IgG1a Fc, a feline IgG1b Fc, a feline IgG2 Fc, a canine IgG1a Fc, a canine IgG1b Fc, or a canine IgG2 Fc. A Fc fragment disclosed herein may be a peptide with the amino acid sequence of SEQ ID NO: 2, SEQ ID NO: 3 or SEQ ID NO: 4, or a sequence having, e.g., at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity to the amino acid sequence of SEQ ID NO: 2, SEQ ID NO: 3 or SEQ ID NO: 4. A Fc fragment disclosed herein may be a peptide with the amino acid sequence of SEQ ID NO: 2 wherein the first 1 to 8 amino acids on the N-terminal end may be absent, SEQ ID NO: 3 wherein the first 1 to 8 amino acids on the N-terminal end may be absent, or SEQ ID NO: 4 wherein the first 1 to 8 amino acids on the N-terminal end may be absent.

In yet other aspect of this embodiment, a Fc fragment disclosed herein may have, e.g., at least 1, at least 2, at least 3, at least 4, at least 5, at least 6, at least 7, at least 8, at least 9, at least 10, at least 11, at least 12, at least 13, at least 14, at least 15, at least 16, at least 17 amino acid additions, substitutions, or deletions to SEQ ID NO: 2, SEQ ID NO: 3 or SEQ ID NO: 4. In still other aspect of this embodiment, a Fc fragment disclosed herein may have, e.g., at most 17, at most 16, at most 15, at most 14, at most 13, at most 12, at most 11, at most 10, at most 9, at most 10, at most 11, at most 12, at most 13, at most 14, at most 15, at most 16, or at most 17 amino acid additions, substitutions, or deletions to SEQ ID NO: 2, SEQ ID NO: 3 or SEQ ID NO: 4. In other aspect of this embodiment, a Fc fragment disclosed herein may have, e.g., 1-17, 1-16, 1-15, 1-14, 1-13, 1-12, 1-10, 1-9, 1-8, 1-7, 1-6, 1-5, 1-4, 1-3, 1-2, 2-17, 2-16, 2-15, 2-4, 2-13, 2-12, 2-10, 2-9, 2-8, 2-7, 2-6, 2-5, 2-4, 2-3, 3-17, 3-16, 3-15, 3-4, 3-13, 3-12, 3-10, 3-9, 3-8, 3-7, 3-6, 3-5, 3-4, 4-17, 4-16, 4-15, 4-14, 4-13, 4-12, 4-10, 4-9, 4-8, 4-7, 4-6, 4-5, 5-17, 5-16, 5-15, 5-14, 5-13, 5-12, 5-10, 5-9, 5-8, 5-7, 5-6, 5-5, 6-17, 6-16, 6-15, 6-14, 6-13, 6-12, 6-10, 6-9, 6-8, 6-7, 7-17, 7-16, 7-15, 7-14, 7-13, 7-12, 7-10, 7-9, 7-8, 8-17, 8-16, 8-15, 8-14, 8-13, 8-12, 8-10, 8-9, 9-17, 9-16, 9-15, 9-14, 9-13, 9-12, 9-10, 10-17, 10-16, 10-15, 10-14, 10-13, 10-12, 11-17, 11-16, 11-15, 11-14, 11-13, 11-12, 12-17, 12-16, 12-15, 12-14, 12-13, 13-17, 13-16, 13-15, 13-14, 14-17, 14-16, 14-15, 15-17, 15-16, or 16-17 amino acid additions, substitutions or deletions to SEQ ID NO: 2, SEQ ID NO: 3 or SEQ ID NO: 4. These additions, substitutions, or deletions may or may not add a glycosylation site. Substitutions may be conservative or non-conservative.

In yet another embodiment, the Fc fragments may be modified to remove its glycosylation sites. In addition, the fusion proteins described herein may also include the addition of glycosylation, a truncated protein (i.e., a protein fragment) or a protein fused, bound or otherwise attached to additional amino acids, nucleotide(s) or nucleotide sequences, aptamers, labels, drugs, antibodies, etc.

The Fc domains may be further modified to remove its N-glycosylation site. In addition, modifications can be made to the Fc domain to further extend half-life in vivo of an antibody molecule or an Fc fusion protein. For example, introduction of mutations T250Q/M428L to a human IgG1 molecule led to a significant increase in the serum half-life of the IgG1 molecule, as disclosed in U.S. Pat. No. 7,217,798. Other mutations have also been made to increase the binding affinity of Fc to FcRN and extend the serum half-life, such as disclosed in U.S. Pat. No. 8,394,925. The present specification further encompasses DNA sequences encoding such Fc fusion proteins, and recombinant plasmids and host cells for expression.

In one embodiment, the Fc fragment is further modified so that the half-life of the fusion protein in vivo is further extended by, e.g., at least 40%, at least 45%, at least 50%, at least 55%, at least 60%, at least 65%, at least 70%, at least 75%, at least 80%, at least 85%, at least 90%, at least 95% or at least 100%. In one aspect of this embodiment, the half-life of the fusion protein is extended by at least 50%, when compared to a fusion protein constructed using the sequence of an un-modified Fc fragment. In a further embodiment, a therapeutic and its variants have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

Figure 2A:
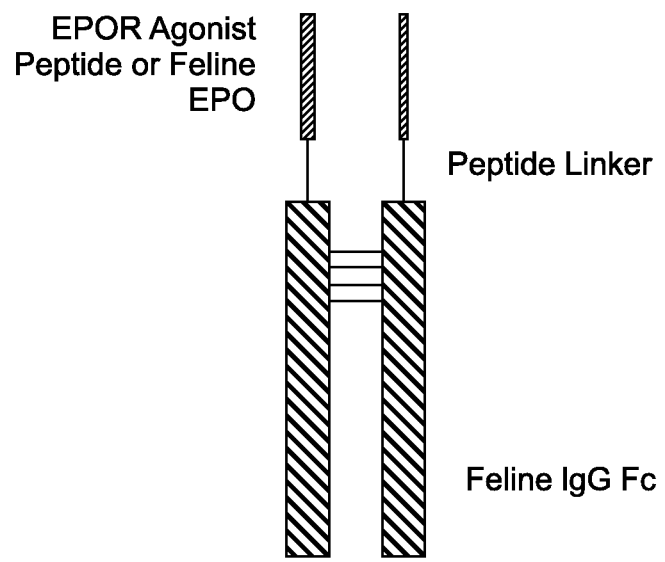
FIG. 2A shows an embodiment disclosed herein where an EpoR agonist peptide is fused, optionally through a peptide linker, to the N-terminals of the Fc domain.
Figure 2B:
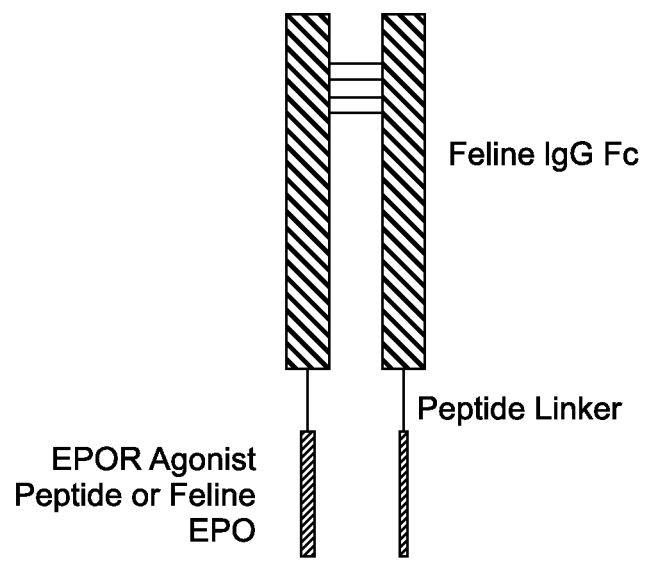
FIG. 2B shows an embodiment disclosed herein where an EpoR agonist peptide is fused, optionally through a peptide linker, to the C-terminals of the Fc domain.

A fusion protein disclosed herein is also optionally is-fused or linked to a Fc fragment disclosed herein using a linker. An example of amino acid linkers includes (GGGGS)n (SEQ ID NO: 7), where n=1, 2, 3, and 4. In one embodiment, a peptide disclosed herein is fused to the N-terminals or the C-terminals of the Fc domain (FIG. 2).

In one embodiment, an EpoR protein agonist disclosed herein is formulated, and used as a medicament, for use in the treatment of NRA caused by conditions including chronic renal failure, cancer, viral infections, and red blood cell aplasia due to antibodies against recombinant human EPO.

The term "isolated proteins" refers to a protein substantially free of cellular material or culture medium when produced by recombinant DNA techniques, or chemical precursors or other chemicals when chemically synthesized.

The term "sequence homology" or "sequence identity" as used herein refers to the percentage of sequence identity between two polypeptide sequences. In order to determine the percentage of identity between two polypeptide sequences, the amino acid sequences of such two sequences are aligned, preferably using the Clustal W algorithm (Thompson, J D, Higgins D G, Gibson T J, 1994, Nucleic Acids Res. 22 (22): 4673-4680), together with BLOSUM 62 scoring matrix (Henikoff S, and Henikoff J. G., 1992, Proc. Natl. Acad. Sci. USA 89: 10915-10919) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (J. Mol. Biol., 1970, 48: 443), as revised by Smith and Waterman (Adv. Appl. Math., 1981, 2: 482) so that the highest order match is obtained between the two sequences and the number of identical amino acids is determined between the two sequences. Other methods to calculate the percentage identity between two amino acid sequences are generally art recognized and include, for example, those described by Carillo and Lipton (SIAM J. Applied Math., 1988, 48:1073) and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux et al., Nucleic Acids Res., 1984, 12: 387) BLASTP, BLASTN and FASTA (Altschul et al., J. Molec. Biol., 1990: 215: 403). In one aspect the present modified non-human mammalian EPO or fusion proteins have at least 70%, at least 75%, at least 80%, at least 85%, at least 87%, at least 90%, at least 91%, at least 92%, at least 93%, at least 94% at least 95%, at least 96%, at least 97%, at least 98%, at least 99% or 100% sequence identity with another sequence, either on a local or a full-length basis.

If on a local basis, the locality is determined by a region of the non-modified or native sequence, or a specifically identified motif of non-modified or native sequence. In one aspect the locality is at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 55, at least 60, at least 65, at least 70, or at least 75 nucleic acids or amino acids of the non-modified or native sequence.

The term "variant" as used herein includes modifications or chemical equivalents of the amino acid and nucleotide sequences disclosed herein that perform substantially the same function as the proteins or nucleic acid molecules disclosed herein in substantially the same way. For example, variants of proteins disclosed herein include, without limitation, conservative amino acid substitutions. Variants of proteins disclosed herein also include additions and deletions to the proteins disclosed herein. In addition, variant peptides and variant nucleotide sequences include analogs and chemical derivatives thereof.

The present modified non-human mammalian erythropoietin or fusion protein may have amino acid additions, deletions, or substitutions. A modified amino acid sequence is a sequence that is different from the native amino acid sequence due to a deletion, an insertion, a non-conservative or conservative substitution or combinations thereof of one or more amino acid residues. In one embodiment, the modification is a point mutation. In one aspect, the modified non-human mammalian erythropoietin does not have a naturally occurring sequence. Similarly, in one aspect, the P of the fusion protein is a non-naturally occurring amino acid sequence.

The amino acid substitutions may be conservative or non-conservative. A "conservative amino acid substitution", as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). The most commonly occurring exchanges are Ala/Ser, Val/Ile, Asp/Glu, Thr/Ser, Ala/Gly, Ala/Thr, Ser/Asn, Ala/Val, Ser/Gly, Ala/Pro, Lys/ Arg, Asp/Asn, Leu/Ile, Leu/Val, Ala/Glu and Asp/Gly, in both directions. Amino acid exchanges in proteins and peptides, which do not generally alter the activity of the proteins or peptides, are known in the art (H. Neurath, R. L. Hill, The Proteins, Academic Press, New York, 1979).

The term "derivative of a peptide" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "nucleic acid sequence" as used herein refers to a sequence of nucleoside or nucleotide monomers consisting of naturally occurring bases, sugars and intersugar (backbone) linkages. The term also includes modified or substituted sequences comprising non-naturally occurring monomers or portions thereof. The nucleic acid sequences disclosed herein may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine.

The present modified non-human mammalian EPO or fusion proteins may made by conventional means, such as recombination. The term "recombinant" as used herein refers to a polypeptide produced through a biological host, selected from a mammalian expression system, an insect cell expression system, a yeast expression system, and a bacterial expression system.

Accordingly, the nucleic acid molecules disclosed herein may be incorporated in a known manner into an appropriate expression vector which ensures good expression of the proteins disclosed herein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule disclosed herein and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The present specification therefore contemplates a recombinant expression vector containing a nucleic acid molecule disclosed herein, or a fragment thereof, and the necessary regulatory sequences for the transcription and translation of the inserted protein-sequence. Suitable regulatory sequences may be derived from a variety of sources, including bacterial, fungal, viral, mammalian, or insect genes (For example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors disclosed herein may also contain a selectable marker gene which facilitates the selection of host cells transformed or transfected with a recombinant molecule disclosed herein. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors disclosed herein and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector disclosed herein. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 3rd Edition, Cold Spring Harbor Laboratory Press, 2001), and other laboratory textbooks.

Suitable host cells include a wide variety of eukaryotic host cells and prokaryotic cells. For example, the proteins disclosed herein may be expressed in yeast cells or mammalian cells. Other suitable host cells can be found in Goeddel, Gene Expression Technology: Methods in Enzymology 185, Academic Press, San Diego, Calif. (1991). In addition, the proteins disclosed herein may be expressed in prokaryotic cells, such as *Escherichia coli* (Zhang et al., Science 303(5656): 371-3 (2004)). In addition, a *Pseudomonas* based expression system such as *Pseudomonas fluorescens* can be used (US Patent Application Publication No. US 2005/0186666, Schneider, Jane C et al.).

Yeast and fungi host cells suitable for carrying out the disclosed methods include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., Embo J. 6:229-234 (1987)), pMFa (Kurjan and Herskowitz, Cell 30:933-943 (1982)), pJRY88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Itoh et al., J. Bacteriology 153: 163 (1983), and Cullen et al. (Bio/Technology 5:369 (1987)).

Mammalian cells suitable for carrying out the disclosed methods include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the proteins disclosed herein may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034).

Insect cells suitable for carrying out the disclosed methods include cells and cell lines from *Bombyx*, *Trichoplusia* or *Spodotera* species. Baculovirus vectors available for expression of proteins in cultured insect cells (SF 9 cells) include the pAc series (Smith et al., Mol. Cell. Biol. 3:2156-2165 (1983)) and the pVL series (Lucklow, V. A., and Summers, M. D., Virology 170:31-39 (1989)). Some baculovirus-insect cell expression systems suitable for expression of the recombinant proteins disclosed herein are described in PCT/US/02442.

Alternatively, the proteins disclosed herein may also be expressed in non-human transgenic animals such as rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866).

The proteins disclosed herein may also be prepared by chemical synthesis using techniques well known in the chemistry of proteins such as solid phase synthesis (Merrifield, J. Am. Chem. Assoc. 85:2149-2154 (1964); Frische et al., J. Pept. Sci. 2(4): 212-22 (1996)) or synthesis in homogenous solution (Houbenweyl, Methods of Organic Chemistry, ed. E. Wansch, Vol. 15 I and II, Thieme, Stuttgart (1987)).

N-terminal or C-terminal fusion proteins comprising the proteins disclosed herein conjugated with other molecules, such as proteins may be prepared by fusing, through recombinant techniques. The resultant fusion proteins contain a protein disclosed herein fused to the selected protein or marker protein as described herein. The recombinant protein disclosed herein may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins which may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Accordingly, the present specification provides a recombinant expression vector comprising the nucleic acid sequences that encode the proteins disclosed herein, such as the light and heavy chain complementarity determining regions, the light and heavy chain variable regions, the binding proteins, such as antibodies and antibody fragments, immunoconjugates disclosed herein and novel isolated proteins disclosed herein. Further, the present specification provides a host cell comprising the recombinant expression vector disclosed herein.

In addition, the present polypeptide sequence may be capable of selective binding to a solid support by including a positively or a negatively charged amino acid sequence, a cysteine-containing amino acid sequence, avidin, streptavidin, a functional fragment of *Staphylococcus* protein A, GST, a His-tag, a FLAG-tag or Lex A. As is described in the appended Examples, the polypeptide disclosed herein exemplified by a single-chain antibody may also be expressed with an N-terminal FLAG-tag and/or C-terminal His-tag that allow for easy purification and detection. The FLAG-tag may include 8 amino acids. However, FLAG-tags comprised of shortened versions of the FLAG used in the appended examples such as the amino acid sequence Asp-Tyr-Lys-Asp (SEQ ID NO: 15) are suitable as well. Thus, the present peptides may be included in kits for the purification of an analyte, or for detection of an analyte in a sample taken from a subject. Thus, the present peptides may also be used for diagnosis of NRA or other conditions.

The term "sample" as used herein refers to any fluid, cell or tissue sample from a subject which can be assayed for an EpoR. That is, any biological tissue or excreted material from an organism. Examples of samples include blood, mucous, sperm, urine, organ tissues, finger and toe nails, hair, skin cells, stool, milk, tears, bile, marrow and tissue samples from organs including the lungs, liver, kidney, heart, bladder, esophagus, stomach, breasts, prostate, arteries, veins, lymph nodes, lymph ducts, tongue, salivary gland, large intestine, small intestine, pituitary gland, pineal gland, thymus, thyroid gland, parathyroid gland, adrenal gland, ovary, oviduct, uterus, vagina, vulva, penis, testis, spleen, brain, spinal cord, nose, pharynx, larynx, trachea, eye, ear, and bowel.

The term "refolding" as used herein refers to the process by which a protein structure assumes its functional shape or conformation. It is the physical process by which a polypeptide folds into its characteristic and functional three-dimensional structure from random coil. It takes place at a basic pH (typically pH 8.0-10.0, preferably pH 8.5-10, more preferably pH 8.5-9.6), a low temperature (typically 0.0° C. to 10.0° C., preferably 2.0° C. to 8.0° C.), preferably with the presence of a redox pair at suitable concentrations, and/or at the presence of oxygen, and/or at the presence of catalyst(s) such as copper ions at suitable concentration.

The present disclosures also relate to the treatment of a subject with the modified non-human mammalian EPO or fusion protein disclosed herein. The term "subject" is those suspected of having anemia, which includes but is not limited to mammals including a cat, a dog, a mouse, a rat, a hamster, a rabbit, a guinea pig, a ruminant, a ferret, a non-human primate, a pig, or other livestock having NRA or having the possibility of NRA. In one embodiment, the subject is a cat, a dog, a mouse, a rat, a hamster, a rabbit, a guinea pig, a ruminant, a ferret, a non-human primate, or a pig. However, any non-human subject to be treated with the fusion proteins or the pharmaceutical composition disclosed herein is included without limitation, in an aspect of this embodiment, the subject is not a human being. In another aspect of this embodiment, the treatment of a subject with the modified non-human mammalian EPO or fusion protein disclosed herein is for a veterinary treatment. The pharmaceutical composition including the novel proteins disclosed herein is administered to a subject suspected of anemia, thereby treating the subject effectively.

Since EPO has been shown to have a mitogenic and chemotactic effect on vascular endothelial cells as well as an effect on central cholinergic neurons (see, e.g., Amagnostou et al. (1990) Proc. Natl. Acad. Sci. USA 87:5978-5982 and Konishi et al. (1993) Brain Res. 609:29-35), the compounds disclosed herein may also find use for the treatment of a variety of vascular disorders in subjects, such as promoting wound healing, growth of collateral coronary blood vessels (such as those that may occur after myocardial infarction), trauma, and post-vascular graft treatment, and a variety of neurological disorders, generally characterized by low absolute levels of acetyl choline or low relative levels of acetyl choline as compared to other neuroactive substances e.g., neurotransmitters.

In still another aspect, the present specification provides a pharmaceutical composition (aka, "therapeutic") for the prevention or treatment of NRA comprising the fusion proteins and modified feline EPO proteins.

The term "formulation" as used herein refers to the modified non-human mammalian EPO and fusion proteins disclosed herein and excipients combined together which can be administered and has the ability to bind to the corresponding receptors and initiate a signal transduction pathway resulting in the desired activity. The formulation can optionally comprise other agents so long as the present modified non-human mammalian EPO or fusion protein retains the ability to bind the corresponding receptors and ligands.

In an embodiment, a first therapeutic is administered to a subject and at a later date, a second therapeutic is administered to the same subject. In an embodiment, a first therapeutic is administered to a subject at the same time as a second therapeutic is administered to the subject.

In aspects of this embodiment, a sustained release therapeutic delivery platform releases a therapeutic disclosed herein with substantially zero order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release therapeutic delivery platform releases a therapeutic disclosed herein with substantially zero order release kinetics over a period of, e.g., at least 7 days after administration, at least 15 days after administration, at least 30 days after administration, at least 45 days after administration, at least 60 days after administration, at least 75 days after administration, or at least 90 days after administration.

In aspects of this embodiment, a sustained release therapeutic delivery platform releases a therapeutic disclosed herein with substantially first order release kinetics over a period of, e.g., about 7 days after administration, about 15 days after administration, about 30 days after administration, about 45 days after administration, about 60 days after administration, about 75 days after administration, or about 90 days after administration. In other aspects of this embodiment, a sustained release therapeutic delivery platform releases a therapeutic disclosed herein with substantially first order release kinetics over a period of, e.g., at least 7 days after administration, at least 15 days after administration, at least 30 days after administration, at least 45 days after administration, at least 60 days after administration, at least 75 days after administration, or at least 90 days after administration.

In an embodiment, a therapeutic disclosed herein in may be in any concentration desired. In aspects of this embodiment, the concentration of a therapeutic disclosed herein may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the concentration of a therapeutic disclosed herein on may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL. The final concentration of a therapeutic disclosed herein in a pharmaceutical composition disclosed herein may be of any concentration desired. In an aspect of this embodiment, the final concentration of a therapeutic in a pharmaceutical composition may be a therapeutically effective amount. In other aspects of this embodiment, the final concentration of a therapeutic in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a cancer therapeutic disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the final concentration of a therapeutic in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

In an aspect, a concentration of a therapeutic disclosed herein typically may be between about 50 mg/mL to about 1,000 mg/mL. In aspects of this embodiment, a therapeutically effective amount of a therapeutic disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

In a further aspect, an amount of a therapeutic disclosed herein typically may be between about 0.01% to about 45% by weight. In aspects of this embodiment, an amount of a therapeutic disclosed herein may be from, e.g., about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, or about 25% to about 30% by weight.

As used herein, the term "prevention" means all of the actions by which the occurrence of the disease is suppressed, restrained or retarded. In the present specification, "prevention" means that the occurrence of anemia is suppressed, restrained or retarded by administration of the conjugates disclosed herein.

As used herein, the term "treatment" means all of the actions by which one or more symptoms of the disease have been alleviated, improved or ameliorated. In the present specification, "treatment" means that the symptoms of NRA are alleviated, improved or ameliorated by administration of the novel proteins disclosed herein.

As used herein, the term "administration" means introduction of an amount of a predetermined substance into a patient by a certain suitable method. The composition disclosed herein may be administered via any of the common routes, as long as it is able to reach a desired tissue, for example, but is not limited to, intraperitoneal, intravenous, intramuscular, subcutaneous, intradermal, oral, topical, intranasal, intrapulmonary, or intrarectal administration. However, since peptides are digested upon oral administration, active ingredients of a composition for oral administration should be coated or formulated for protection against degradation in the stomach.

The composition disclosed herein may be formulated into a variety of dosage forms in combination with pharmaceutically acceptable carriers, binders, lubricants, disintegrants, excipients, diluents, solubilizers, dispersing agents, stabilizers, suspending agents, colorants, flavorants, buffering agents, preserving agents, anti-oxidants, analgesics, solubilizers, isotonic agents, and base materials.

For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multi-dose container. The pharmaceutical composition may also be formulated into solutions, suspensions, tablets, pills, capsules and long-acting preparations.

Further, the pharmaceutical composition disclosed herein may have any formulation selected from the group consisting of tablets, pills, powders, granules, capsules, suspensions, liquids for internal use, emulsions, syrups, sterile aqueous solutions, non-aqueous solvents, lyophilized formulations and suppositories.

The pharmaceutical composition disclosed herein may further include a pharmaceutically acceptable excipient or diluent. As used herein, the term "pharmaceutically acceptable" means that the composition is sufficient to achieve the therapeutic effects without deleterious side effects, and may be readily determined depending on the type of the diseases, the subject's species, age, body weight, health conditions, gender, and drug sensitivity, administration route, administration mode, administration frequency, duration of treatment, drugs used in combination or coincident with the composition disclosed herein, and other factors known in medicine.

For oral administration, the pharmaceutical composition may include, but is not limited to, a carrier, a binder, a lubricant, a disintegrant, an excipient, a diluent, a solubilizer, a dispersing agent, a stabilizer, a suspending agent, a colorant, and a flavorant. For injectable preparations, the pharmaceutical composition may include a buffering agent, a preserving agent, an analgesic, a solubilizer, an isotonic agent, and a stabilizer. For preparations for topical administration, the carrier may include a base, an excipient, a lubricant, and a preserving agent.

Examples of the carrier for the pharmaceutical compositions include physiological saline, organic solvents, lactose, dextrose, sucrose, sorbitol, mannitol, xylitol; erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the excipient or diluent for pharmaceutical formulations may further include fillers, anti-coagulating agents, solubilizer, antioxidants, lubricants, humectants, flavorants, and antiseptics. In one embodiment, the pharmaceutical composition may be obtained by blending with a variety of pharmaceutically acceptable carriers. In order to increase the stability or absorptivity, carbohydrates such as glucose, sucrose or dextrans, antioxidants such as ascorbic acid or glutathione, chelating agents, low molecular weight proteins or other stabilizers may be used.

Further, the pharmaceutical composition may be formulated into a single dosage form suitable for the subject's body. For example, the pharmaceutical composition is formulated into a preparation useful for peptide drugs according to the typical method in the pharmaceutical field so as to be administered by an oral or parenteral route such as through skin, intravenous, intramuscular, intra-arterial, intramedullary, intramedullary, intraventricular, pulmonary, transdermal, subcutaneous, intraperitoneal, intranasal, intracolonic, topical, sublingual, vaginal, or rectal administration, but is not limited thereto.

The administration dose and frequency of the pharmaceutical composition disclosed herein are determined by the type of active ingredient, together with various factors such as the disease to be treated, administration route, subject's species, age, gender, and body weight, and disease severity.

Timing of Administration Methods disclosed herein include administration of the modified non-human mammalian EPO or fusion proteins disclosed herein prior to, substantially contemporaneously with or after the subject has been diagnosed with NRA, and administration prior to, substantially contemporaneously with or after a pathology or a development of one or more adverse symptoms of NRA or pathologies caused by NRA. Methods, compositions and uses disclosed herein also include administration of the modified non-human mammalian EPO or fusion proteins to a subject prior to, substantially contemporaneously with or following the identification of an adverse symptom, disorder, illness or disease caused by or associated with NRA, or pathology resulting from NRA. A subject with NRA may have NRA or present symptoms of NRA over a period of 1-5, 5-10, 10-20, 20-30, 30-50, 50-100 hours, days, weeks, months, or years.

The compositions disclosed herein can be combined with any compound, agent, drug, treatment or other therapeutic regimen or protocol having a desired therapeutic, beneficial, additive, synergistic or complementary activity or effect. Exemplary combination compositions and treatments include second actives such as, e.g., drugs or agents related to the treatment of bone marrow disease, tick disease, abscesses, cancer, kidney failure, toxic chemical exposure, radiation exposure, lead poisoning, and inherited NRA. Such drugs, agents, treatments and therapies can be administered or performed prior to, substantially contemporaneously with or following any other method disclosed herein, for example, a therapeutic method of treating a subject for an NRA thereto, or a method of prophylactic treatment of a subject for NRA. Moreover, the pharmaceutical composition may be administered alone or in combination or coincident with other pharmaceutical formulations showing prophylactic or therapeutic effects on anemia, especially NRA.

The compositions disclosed herein can be administered as a combination composition, or administered separately, such as concurrently or in series or sequentially (prior to or following) administering a second active, to an individual. The present specification therefore provides combinations in which a method or use is used in a combination with any compound, agent, drug, therapeutic regimen, treatment protocol, process, remedy or composition, such as drugs or agents related to the treatment of bone marrow disease, tick disease, abscesses, cancer, kidney failure, toxic chemical exposure, radiation exposure, lead poisoning, and inherited NRA. The compound, agent, drug, therapeutic regimen, treatment protocol, process, remedy or composition can be administered or performed prior to, substantially contemporaneously with or following administration of one or more of the present modified non-human mammalian EPO or fusion proteins or subsequences, portions or modifications thereof, or a nucleic acid encoding all or a portion of the present modified non-human mammalian EPO or fusion proteins, subsequence, portion or modification thereof, to a subject. Specific non-limiting examples of combination embodiments therefore include the foregoing or other compound, agent, drug, therapeutic regimen, treatment protocol, process, remedy or composition.

Single Dose/Period of Time The total effective dose of the composition disclosed herein may be administered to a subject in a single dose, or may be administered for a period of time in multiple doses according to a fractionated treatment protocol. For instance, the dose may be determined as a total dose over the lifetime of the subject, a total dose over the expected treatment period, a total monthly dose, a total weekly dose, or a total daily dose.

In an embodiment, the period of administration of a modified non-human mammalian EPO or fusion proteins disclosed herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Dosing can be single dosage or cumulative (serial dosing), and can be readily determined by one skilled in the art. For instance, treatment of anemia may comprise a one-time administration of a sufficient dose of a composition disclosed herein. As a non-limiting example, a sufficient dose of a composition disclosed herein can be administered once to a subject, e.g., as a single injection or deposition or a single oral administration. Alternatively, treatment may comprise a one-time administration of a sufficient dose of a composition disclosed herein carried out over a range of time periods, such as, e.g., daily, once every few days, weekly, monthly or yearly. As a non-limiting example, an antigen or a composition disclosed herein can be administered once or twice weekly to a subject. The timing of administration can vary from subject to subject, depending upon such factors as the severity of the subject's symptoms. For example, a sufficient dose of an antigen or a composition disclosed herein can be administered to a subject once a month for an indefinite period of time, or until the subject no longer requires therapy. A person of ordinary skill in the art will recognize that the condition of the subject can be monitored throughout the course of treatment and that the sufficient amount of a composition disclosed herein that is administered can be adjusted accordingly.

Total Daily Dose In one embodiment the total daily dose of the modified non-human mammalian EPO or fusion protein disclosed herein may be approximately 0.01 µg to 5 mg per 1 kg of body weight of a patient (aka µg/kg or g/kg). In one embodiment, the total daily dose is at least 0.01 µg/kg, at least 0.05 gag, at least 0.1 gag, at least 0.5 gag, at least 1 µg/kg, at least 5 µg/kg, at least 0.01 mg/kg, at least 0.05 mg/kg, at least 0.1 mg/kg, at least 0.5 mg/kg, at least 1 mg/kg, at least 1.5 mg/kg, at least 2 mg/kg, at least 2.5 mg/kg, at least 3 mg/kg, at least 3.5, mg/kg, at least 4 mg/kg, at least 4.5 mg/kg, or at least 5 mg/kg. In one aspect, the maximum daily dose is at most 5 mg/kg, at most 4.5 mg/kg, at most 4.0 mg/kg, at most 3.5 mg/kg, at most 3 mg/kg, at most 2.5 mg/kg, at most 2 mg/kg, at most 1.5 mg/kg, at most 1 mg/kg, at most 0.5 mg/kg, at most 0.1 mg/kg, at most 0.05 mg/kg, at most 10 gag, at most 5 µg/kg, at most 1 gag, at most 0.05 gag, or at most 0.1 µg/kg. In yet another aspect the daily dose of the modified non-human mammalian EPO or fusion protein disclosed herein may be approximately 0.05 µg/kg to 5 mg/kg, 0.1 µg/kg to 5 mg/kg, 1 µg/kg to 5 mg/kg, 50 µg/kg to 5 mg/kg, 0.1 mg/kg to 5 mg/kg, or 1 mg/kg to 5 mg/kg. In an even further aspect the daily dose of the modified non-human mammalian EPO or fusion protein may be approximately 0.01 µg/kg to 2 mg/kg, 0.05 µg/kg to 2 mg/kg, 0.1 µg/kg to 2 mg/kg, 1 µg/kg to 2 mg/kg, 5 µg/kg to 2 mg/kg, 10 µg/kg to 2 mg/kg, 50 µg/kg to 2 mg/kg, 100 µg/kg to 2 mg/kg, 0.5 mg/kg to 2 mg/kg, or 1 mg/kg to 2 mg/kg. In still other aspects of this embodiment, a sufficient amount of a modified non-human mammalian EPO or fusion protein disclosed herein is the dosage sufficient to reduce a symptom associated with anemia for, e.g., at least one week, at least one month, at least two months, at least three months, at least four months, at least five months, at least six months, at least seven months, at least eight months, at least nine months, at least ten months, at least eleven months, or at least twelve months.

However, the effective dose of the modified non-human mammalian EPO or fusion protein is determined considering various factors including subject's species, age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition disclosed herein. The pharmaceutical composition disclosed herein is not particularly limited to the formulation, and administration route and mode, as long as it shows a beneficial effects.

The pharmaceutical composition disclosed herein is expected to have longer in vivo duration of efficacy and titer, thereby remarkably reducing the number and frequency of administration thereof when compared to administration of native EPO (i.e., EPO having the full-length amino acid sequence of the naturally occurring EPO amino acid sequence). In one embodiment, a composition disclosed herein and its derivatives or variants have half-lives of 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 7 days, 1 week, 2 weeks, 3 weeks, 4 weeks, one month, two months, three months, four months or more.

In an embodiment, an individual is provided a treatment protocol wherein a pharmaceutical composition is to be administered to a subject on a periodic schedule, wherein the individual is informed by electronic notification to administer the therapeutic on a period schedule. In an aspect of this embodiment, the electronic notification is by email, text, instant messaging or by another electronic notification method. In an embodiment, an individual is informed to administer the presently disclosed therapeutic on a period schedule through receipt of a telephone call, postal mail, overnight express (including, without limitation, FedEx and UPS) or other method of notification.

Aspects of the present specification can also be described as follows:

1. A modified non-human mammalian erythropoietin comprising a mammalian erythropoietin sequence and at least one added or relocated glycosylation site.
2. The modified non-human mammalian erythropoietin according to embodiment 1, wherein the mammalian erythropoietin comprises an amino acid sequence having at least 90% sequence homology to a sequence selected from the group consisting of: feline erythropoietin, or canine erythropoietin.
3. The modified non-human mammalian erythropoietin according to embodiment 1 or embodiment 2, wherein the mammalian erythropoietin comprises an amino acid sequence having at least 95% sequence identity to an amino acid sequence of a feline erythropoietin or a canine erythropoietin.
4. The modified non-human mammalian erythropoietin according to any one of embodiments 1-3, wherein the mammalian erythropoietin comprises an amino acid sequence having at least 90%, at least 95%, at least 96%, at least 97%, at least 98% or at least 99% sequence identity to SEQ ID NO: 5, SEQ ID NO: 6, SEQ ID NO: 10 or SEQ ID NO: 11, wherein Xaa at position 18 of SEQ ID NO: 5 or SEQ ID NO: 6 is selected from E or G; and Xaa at position 116 of SEQ ID NO: 5 or SEQ ID NO: 6 is K or absent.
5. The modified non-human mammalian erythropoietin according to any one of embodiments 1-4, wherein the mammalian erythropoietin comprises from about 3 to about 5, about 3 to about 8, about 3 to about 10, about 3 to about 12, about 3 to about 15 or about 3 to about 17 amino acid additions, deletions, or substitutions.
6. The modified non-human mammalian erythropoietin according to any one of embodiments 1-5, wherein the glycosylation site has the structure Asn-Xaa-Ser/Thr, wherein Xaa is any amino acid.
7. The modified non-human mammalian erythropoietin according to any one of embodiments 1-6, wherein the glycosylation site is a site for the attachment of an N-linked carbohydrate chain.
8. The modified non-human mammalian erythropoietin according to any one of embodiments 1-7, wherein the glycosylation site comprises a serine, threonine, hydroxyproline, or hydroxylysine.
9. The modified non-human mammalian erythropoietin according to any one of embodiments 1-8, wherein the glycosylation site is a site for the attachment of an O-linked carbohydrate chain.
10. The modified non-human mammalian erythropoietin according to any one of embodiments 1-9, wherein the glycosylation site is located at the carboxy terminal region of the mammalian erythropoietin.

11. The modified non-human mammalian erythropoietin according to any one of embodiments 1-9, wherein the glycosylation site is inserted between amino acids in the mammalian erythropoietin sequence.

12. The modified non-human mammalian erythropoietin according to any one of embodiments 1-11, wherein the glycosylation site further comprises a fragment of human chorionic gonadotropin.

13. The modified non-human mammalian erythropoietin according to embodiment 12, wherein the fragment of human chorionic gonadotropin is SEQ ID NO: 8 or an amino acid sequence having at least 90%, at least 95%, at least 96%, at least 97%, at least 98% or at least 99% sequence identity to SEQ ID NO: 8, or an amino acid sequence having 1, 2, 3, 4, 5, 1-2, 1-3, 1-4, 1-5, 2-3, 2-4, 2-5, 3-4, 3-5, or 4-5 amino acid additions, deletions or substitutions to SEQ ID NO: 8.

14. The modified non-human mammalian erythropoietin according to any one of embodiments 1-13, further comprising at least one additional carbohydrate chain attached thereto.

15. The modified non-human mammalian erythropoietin according to any one of embodiments 1-14, wherein the mammalian erythropoietin is feline erythropoietin having the amino acid sequence of SEQ ID NO: 5 or SEQ ID NO: 6, wherein Xaa at position 18 is selected from E or G; and Xaa at position 116 is K or absent, or a sequence having at least 90%, at least 95%, at least 96%, at least 97%, at least 98% or at least 99% sequence identity to SEQ ID NO: 5 or SEQ ID NO: 6, wherein Xaa at position 18 is selected from E or G; and Xaa at position 116 is K or absent, and wherein in SEQ ID NO: 5 or SEQ ID NO: 6 an asparagine residue is substituted for the amino acid residue at any one or more of positions 30, 51, 57, 69, 88, 89, 137, or 139.

16. The modified non-human mammalian erythropoietin according to any one of embodiments 1-15, wherein the mammalian erythropoietin is feline erythropoietin having the amino acid sequence of SEQ ID NO: 5 or SEQ ID NO: 6, wherein Xaa at position 18 is selected from E or G; and Xaa at position 116 is K or absent, or a sequence having at least 90%, at least 95%, at least 96%, at least 97%, at least 98% or at least 99% sequence identity to SEQ ID NO: 5 or SEQ ID NO: 6, wherein Xaa at position 18 is selected from E or G; and Xaa at position 116 is K or absent, and wherein in SEQ ID NO: 5 or SEQ ID NO: 6 either a serine or a threonine residue is substituted for the amino acid residue at position 126.

17. The modified non-human mammalian erythropoietin according to any one of embodiments 1-14, wherein the mammalian erythropoietin is feline erythropoietin having the amino acid sequence of SEQ ID NO: 5 or SEQ ID NO: 6, wherein Xaa at position 18 is selected from E or G; and Xaa at position 116 is K or absent, or a sequence having at least 90%, at least 95%, at least 96%, at least 97%, at least 98% or at least 99% sequence identity to SEQ ID NO: 5 or SEQ ID NO: 6, wherein Xaa at position 18 is selected from E or G; and Xaa at position 116 is K or absent, and wherein in SEQ ID NO: 5 or SEQ ID NO: 6 one or more of the following amino acid substitution sets is present: $Asn^{39}$ and $Thr^{32}$; $Asn^{51}$ and $Thr^{53}$; $Asn^{57}$, $Thr^{59}$ and $Asn^{69}$; $Asn^{69}$ and $Thr^{71}$; $Ser^{68}$, $Asn^{69}$ and $Thr^{71}$; $Val^{87}$ and $Asn^{88}$; $Ser^{87}$ and $Asn^{88}$; $Ser^{87}$, $Asn^{88}$ and $Gly^{89}$; $Ser^{87}$, $Asn^{88}$ and $Thr^{92}$; $Ser^{87}$, $Asn^{88}$ and $Ala^{163}$; $Asn^{69}$, $Thr^{71}$, $Ser^{87}$ and $Asn^{88}$; $Asn^{30}$, $Thr^{32}$, $Val^{87}$ and $Asn^{88}$; $Asn^{89}$, $Ile^{99}$ and $Thr^{91}$; $Ser^{87}$, $Asn^{89}$, $Ile^{99}$ and $Thr^{91}$; $Asn^{137}$ and $Thr^{139}$; $Asn^{139}$ and $Thr^{141}$; $Thr^{126}$; $Pro^{125}$ and $Thr^{126}$; or any combination thereof.

18. The modified non-human mammalian erythropoietin according to embodiment 17, wherein the mammalian erythropoietin is feline erythropoietin having the amino acid sequence of SEQ ID NO: 5 or SEQ ID NO: 6, wherein Xaa at position 18 is selected from E or G; and Xaa at position 116 is K or absent, or a sequence having at least 90%, at least 95%, at least 96%, at least 97%, at least 98% or at least 99% sequence identity to SEQ ID NO: 5 or SEQ ID NO: 6, wherein Xaa at position 18 is selected from E or G; and Xaa at position 116 is K or absent, and wherein in SEQ ID NO: 5 or SEQ ID NO: 6 one or more of the following substitution sets is present: $Ser^{87}$ and $Asn^{88}$; and/or $Asn^{30}$, $Thr^{32}$, $Val^{87}$ and $Asn^{88}$.

19. The modified non-human mammalian erythropoietin according to embodiment 17, wherein the mammalian erythropoietin is feline erythropoietin having the amino acid sequence of SEQ ID NO: 5 or SEQ ID NO: 6, wherein Xaa at position 18 is selected from E or G; and Xaa at position 116 is K or absent, with one of the following amino acid substitution sets is present: $Gln^{24}$, $Ser^{87}$ and $Asn^{88}$; $Gln^{38}$, $Ser^{87}$ and $Asn^{88}$; or $Gln^{83}$, $Ser^{87}$ and $Asn^{88}$.

20. The modified non-human mammalian erythropoietin according to any one of embodiments 1-14, wherein the mammalian erythropoietin is feline erythropoietin of SEQ ID NO: 5 or SEQ ID NO: 6, wherein Xaa at position 18 is selected from E or G; and Xaa at position 116 is K or absent, modified by deleting one or more of the glycosylation sites that attach to N linked carbohydrate chains and by adding a glycosylation site that attaches to an N linked carbohydrate chain at amino acid position 88 of SEQ ID NO: 5 or SEQ ID NO: 6.

21. The modified non-human mammalian erythropoietin according to any one of embodiments 1-14, wherein the mammalian erythropoietin is canine erythropoietin having the amino acid sequence of SEQ ID NO: 10 or SEQ ID NO: 11, or a sequence having at least 90%, at least 95%, at least 96%, at least 97%, at least 98% or at least 99% sequence identity to SEQ ID NO: 10 or SEQ ID NO: 11, wherein in SEQ ID NO: 10 an asparagine residue is substituted for the amino acid residue at any one or more of positions 30, 51, 57, 69, 88, 89, 137, or 139 and wherein in SEQ ID NO: 11 an asparagine residue is substituted for the amino acid residue at any one or more of positions 56, 77, 83, 95, 114, 115, 163, or 165.

22. The modified non-human mammalian erythropoietin according to any one of embodiments 1-14 and 21, wherein the mammalian erythropoietin is canine erythropoietin having the amino acid sequence of SEQ ID NO: 10 or SEQ ID NO: 11, or a sequence having at least 90%, at least 95%, at least 96%, at least 97%, at least 98% or at least 99% sequence identity to SEQ ID NO: 10 or SEQ ID NO: 11, wherein in SEQ ID NO: 10 either a serine or threonine residue is substituted for the amino acid residue at position 126; and wherein in SEQ ID NO: 11 either a serine or threonine residue is substituted for the amino acid residue at position 152.

23. The modified non-human mammalian erythropoietin according to any one of embodiments 1-14, wherein the mammalian erythropoietin is canine erythropoietin having the amino acid sequence of SEQ ID NO: 10 or SEQ ID NO: 11, or a sequence having at least 90%, at least 95%, at least 96%, at least 97%, at least 98% or at least 99% sequence identity to SEQ ID NO: 10 or SEQ ID NO:

11, wherein in SEQ ID NO: 10 one or more of the following amino acid substitution sets is present: $Asn^{30}$ and $Thr^{32}$; $Asn^{51}$ and $Thr^{53}$; $Asn^{57}$ and $Thr^{59}$; $Asn^{69}$; $Asn^{69}$ and $Thr^{71}$; $Ser^{88}$, $Asn^{69}$ and $Thr^{71}$; $Val^{87}$ and $Asn^{88}$; $Ser^{87}$ and $Asn^{88}$; $Ser^{87}$, $Asn^{88}$ and $Gly^{88}$; $Ser^{87}$, $Asn^{88}$ and $Thr^{92}$; $Ser^{87}$, $Asn^{88}$ and $Ala^{163}$; $Asn^{69}$, $Thr^{71}$, $Ser^{87}$ and $Asn^{88}$; $Asn^{30}$, $Thr^{32}$, $Val^{87}$ and $Asn^{88}$; $Asn^{89}$, $Ile^{90}$ and $Thr^{91}$; $Ser^{87}$, $Asn^{89}$, $Ile^{90}$ and $Thr^{91}$; $Asn^{137}$ and $Thr^{139}$; $Asn^{139}$ and $Thr^{141}$; $Thr^{126}$; and/or $Pro^{125}$ and $Thr^{126}$; and wherein in SEQ ID NO: 11 one or more of the following amino acid substitution sets is present: $Asn^{88}$ and $Thr^{58}$; $Asn^{77}$ and $Thr^{79}$; $Asn^{83}$ and $Thr^{85}$; $Asn^{69}$; $Asn^{95}$ and $Thr^{97}$; $Ser^{84}$, $Asn^{95}$ and $Thr^{97}$; $Val^{113}$ and $Asn^{114}$, $Ser^{113}$ and $Asn^{114}$; $Ser^{113}$, $Asn^{114}$ and $Gly^{115}$; $Ser^{113}$, $Asn^{114}$ and $Thr^{118}$; $Ser^{113}$, $Asn^{114}$ and $Ala^{189}$; $Asn^{95}$, $Thr^{97}$, $Ser^{113}$ and $Asn^{114}$; $Asn^{56}$, $Thr^{58}$, $Val^{113}$ and $Asn^{114}$; $Asn^{115}$, $Ile^{116}$ and $Thr^{117}$; $Ser^{113}$, $Asn^{115}$, $Ile^{116}$ and $Thr^{117}$; $Asn^{163}$ and $Thr^{165}$; $Asn^{165}$ and $Thr^{167}$; $Thr^{152}$; and/or $Pro^{151}$ and $Thr^{152}$.

24. The modified non-human mammalian erythropoietin according to embodiment 23, wherein the mammalian erythropoietin is a canine erythropoietin having the amino acid sequence of SEQ ID NO: 10 or SEQ ID NO: 11, or a sequence having at least 90%, at least 95%, at least 96%, at least 97%, at least 98% or at least 99% sequence identity to SEQ ID NO: 10 or SEQ ID NO: 11, wherein in SEQ ID NO: 10 one or more of the following substitution sets is present: $Ser^{87}$ and $Asn^{88}$ and/or $Asn^{30}$, $Thr^{32}$, $Val^{87}$ and $Asn^{88}$; and wherein in SEQ ID NO: 11 one or more of the following substitution sets is present: $Ser^{113}$ and $Asn^{114}$ and/or $Asn^{56}$, $Thr^{58}$, $Val^{113}$ and $Asn^{114}$.

25. The modified non-human mammalian erythropoietin according to embodiment 23, wherein the mammalian erythropoietin is a canine erythropoietin having the amino acid sequence of SEQ ID NO: 10 with one of the following amino acid substitution sets present: $Gln^{24}$, $Ser^{87}$ and $Asn^{88}$; $Gln^{38}$, $Ser^{87}$ and $Asn^{88}$; or $Gln^{83}$, $Ser^{87}$ and $Asn^{88}$; or having the amino acid sequence of SEQ ID NO: 11 with one of the following amino acid substitution sets present: $Gln^{50}$, $Ser^{113}$ and $Asn^{114}$; $Gln^{64}$, $Ser^{113}$ and $Asn^{114}$; or $Gln^{109}$, $Ser^{113}$ and $Asn^{114}$.

26. The modified non-human mammalian erythropoietin according to any one of embodiments 1-14, wherein the mammalian erythropoietin is canine erythropoietin of SEQ ID NO: 10 or SEQ ID NO: 11, modified by deleting one or more of the glycosylation sites that attach to N linked carbohydrate chains and by adding a glycosylation site that attaches to an N linked carbohydrate chain at amino acid position 88 of SEQ ID NO: 10 or SEQ ID NO: 11.

27. A nucleic acid sequence encoding a modified non-human mammalian erythropoietin comprising a mammalian erythropoietin sequence and at least one added or relocated glycosylation site.

27. A nucleic acid sequence encoding a modified non-human mammalian erythropoietin as defined in any one of embodiments 1-27.

28. A nucleic acid sequence encoding a modified feline erythropoietin comprising the amino acid sequence of SEQ ID NO: 5, SEQ ID NO: 6, SEQ ID NO: 10 or SEQ ID NO: 11 or encoding an amino acid sequence having at least 90%, at least 95%, at least 96%, at least 97%, at least 98% or at least 99% sequence identity to SEQ ID NO: 5, SEQ ID NO: 6, SEQ ID NO: 10 or SEQ ID NO: 11.

29. A vector comprising
  a) a nucleic acid sequence encoding a modified non-human mammalian erythropoietin comprising a mammalian erythropoietin sequence and at least one added or relocated glycosylation site, and
  b) a promoter operatively linked to the nucleic acid sequence.

30. A vector comprising
  a) a nucleic acid sequence encoding the amino acid sequence for a modified non-human mammalian erythropoietin as defined in any one of embodiments 1-26 or a nucleic acid sequence as defined in embodiments 27-28, and
  b) a promoter operatively linked to the nucleic acid sequence.

31. A host cell comprising the vector of embodiment 29 or embodiment 30.

32. A composition comprising
  a) a modified non-human mammalian erythropoietin comprising a mammalian erythropoietin sequence and at least one added or relocated glycosylation site, and
  b) a pharmaceutically acceptable diluent, adjuvant, or carrier.

33. A composition comprising
  a) a modified non-human mammalian erythropoietin as defined in any one of embodiments 1-26 or a vector as defined in embodiment 29 or embodiment 30, and
  b) a pharmaceutically acceptable diluent, adjuvant, or carrier.

34. Use of a modified non-human mammalian erythropoietin comprising a mammalian erythropoietin sequence and at least one added or relocated glycosylation site in the manufacture of a medicament for the treatment of non-regenerative anemia (NRA).

35. Use of a modified non-human mammalian erythropoietin as defined in any one of embodiments 1-26 or a vector as defined in embodiment 29 or embodiment 30 in the manufacture of a medicament for the treatment of non-regenerative anemia (NRA).

36. A method of treating non regenerative anemia (NRA) in a mammal comprising administering to a subject in need thereof an effective amount of a modified non-human mammalian erythropoietin comprising a mammalian erythropoietin sequence and at least one added or relocated glycosylation site or a composition comprising a modified non-human mammalian erythropoietin comprising a mammalian erythropoietin sequence and at least one added or relocated glycosylation site.

37. A method of treating non regenerative anemia (NRA) in a mammal comprising administering to a subject in need thereof an effective amount of a modified non-human mammalian erythropoietin as defined in any one of embodiments 1-26 or a composition as defined in embodiment 32 or embodiment 33.

38. Use of a modified non-human mammalian erythropoietin comprising a mammalian erythropoietin sequence and at least one added or relocated glycosylation site for the treatment of non-regenerative anemia (NRA).

39. Use of a modified non-human mammalian erythropoietin as defined in any one of embodiments 1-26 or a composition as defined in embodiment 32 or embodiment 33 for the treatment of non-regenerative anemia (NRA).

40. The method of embodiment 34 or embodiment 35 or the use of embodiment 38 or embodiment 39, wherein the mammal is a cat, a dog, a mouse, a rat, a hamster, a rabbit, a guinea pig, a ruminant, a ferret, a non-human primate, or a pig.

41. A fusion protein, comprising a peptide, a linker and an Fc fragment, wherein:

a) the peptide is SEQ ID NO: 1, an amino acid sequence having at least 90%, at least 95%, at least 96%, at least 97%, at least 98% or at least 99% sequence identity to SEQ ID NO: 1, a feline EPO with the amino acid sequence SEQ ID NO: 5 or SEQ ID NO: 6, wherein Xaa at position 18 is selected from E or G; and Xaa at position 116 is K or absent, a sequence having at least 90%, at least 95%, at least 96%, at least 97%, at least 98% or at least 99% sequence identity to SEQ ID NO: 5 or SEQ ID NO: 6, wherein Xaa at position 18 is selected from E or G; and Xaa at position 116 is K or absent, a canine EPO with the amino acid sequence SEQ ID NO: 10 or SEQ ID NO: 11, or a sequence having at least 90%, at least 95%, at least 96%, at least 97%, at least 98% or at least 99% sequence identity to SEQ ID NO: 10 or SEQ ID NO: 11; and b) the Fc fragment has an amino acid sequence of SEQ ID NO: 2, SEQ ID NO: 3 or SEQ ID NO: 4, or a sequence having at least 90%, at least 95%, at least 96%, at least 97%, at least 98% or at least 99% sequence identity to SEQ ID NO: 2, SEQ ID NO: 3 or SEQ ID NO: 4;

wherein the peptide is fused, through linker, to the Fc fragment.

42. The fusion protein according to embodiment 41, wherein the C terminus of the peptide is fused through the linker to the N terminus of the Fc fragment.

43. The fusion protein according to embodiment 42, wherein the N terminus of the peptide is fused through the linker to the C terminus of the Fc fragment.

44. A nucleic acid sequence encoding the fusion protein of any one of embodiments 40-42.

45. A vector comprising the nucleic acid sequence according to embodiment 44 and a promoter operatively linked to the nucleic acid sequence.

46. A host cell comprising the vector of embodiment 45.

47. A composition comprising:
   a) a fusion protein as defined in any one of embodiments 40-42 or a vector as defined in embodiment 45, and
   b) a pharmaceutically acceptable diluent, adjuvant, or carrier.

48. Use of a fusion protein as defined in any one of embodiments 40-3429 or a vector as defined in embodiment 45 in the manufacture of a medicament for the treatment of non-regenerative anemia (NRA).

49. A method of treating non regenerative anemia (NRA) in a mammal comprising administering to a subject in need thereof an effective amount of a fusion protein as defined in any one of embodiments 37-39 or a composition as defined in embodiment 47.

50. Use of a fusion protein as defined in any one of embodiments 40-3429 or a composition as defined in embodiment 47 for the treatment of non-regenerative anemia (NRA).

51. The method of embodiment 49 or the use of embodiment 50, wherein the mammal is a cat, a dog, a mouse, a rat, a hamster, a rabbit, a guinea pig, a ruminant, a ferret, a non-human primate, or a pig.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods or uses of treating a disorder disclosed herein.

Example 1

Production of Modified Feline EPO

DNA for modified feline EPO having the modifications $Val^{87}Asn^{88}$ was synthesized (SEQ ID NO: 14) and cloned into a bacterial expression vector. The complete expression construct comprising the modified feline EPO DNA gene (named as ASKBH01) was confirmed by DNA sequencing. The expression construct was amplified by transforming into DH10B *E. coli* and culturing the cells overnight. DNA for the expression construct was prepared and purified by endo-free plasmid kit (from QIAGEN®).

Cell lines stably expressing a modified Feline EPO protein were obtained by transfecting the expression construct into $GS^{-/-}$ Chinese hamster ovarian cells (CHO) by electroporation and screening for transfected CHO cells using a selective culture medium without glutamine (EX-CELL® CD CHO Fusion Growth Medium). In this manner 32 stable minipools were established and the leading mini-pool was selected based on expression level in batch and fed-batch cultures. FIG. 3 shows ELISA titer results of the batch cell culture during the 1st round of batch culture clone selection. Single cloning was performed by limited dilution and using clone media, two leading single clones out of 132 positive clones (in total 960 wells) were selected based on productivity and cell growth in batch and fed-batch culture. The lead clones were expanded and seeded at $0.5 \times 10^6$ cells/mL, total 300 mL in 2 L shake flasks, and the cells were cultured at 37° C., 5% $CO_2$, 70% HMR conditions and shaking at 120 rpm. The cultures were fed by using 5% Acti CHO® Feed A+0.5% Feed B (from GE Health) on Day 3, 6, 7, 8 and 9. The cell viability, viable cell density were monitored every other day, the cultures were harvested on Day 11. The cell growth profile, viability and titer are shown in FIG. 4.

Modified Feline EPO protein was harvested by clarifying approximately 600 mL of the cultured cell medium through centrifugation at 2000 rpm for 10 minutes followed by filtration. The clarified supernant was concentrated to approximately 100 mL and buffer exchanged into 10 mM Tris (pH 7.1). A Pellicone II UF membrane with 30 kDa molecular weight cut-off was used for this UFDF step. The UFDF pool was aliquoted and frozen at −80° C. until further purification.

The UFDF pool containing the modified feline EPO was thawed and loaded to a column packed with Q sepahrose FF resin at neutral pH. The column has a diameter of 2 cm and a bed height of approximately 1.5 cm. The column was washed with 10 mM Tris, pH 7.1, followed by a 2nd wash with 2 mM acetic acid, 1 mM glycine, 6 M urea, 20 micoM CuSO4, pH 4.8 to remove host cell impurities and feline EPO isoforms with approximately 7 sialic acids or less. The column was further washed with 40 mM acetic acid, 1 mM glycine, 6 M urea, 20 micoM CuSO4, pH 4.0. This step removed additional cell impurities and feline EPO isoforms containing approximately 8 to approximately 12 sialic acids. The column was then eluted with 10 mM Tris, 140 mM NaCl, 20 micoM CuSO4, pH 7.1 to elute the modified feline EPO isoforms containing more than 12 sialic acids. Chromatography and SDS-PAGE analysis showed that isoforms containing more than 12 sialic acids were expressed at dominant level comparing to the fractions presumably containing the modified feline EPO with lower levels of sialic acids.

The elution pool containing 12 or more sialic acids is further purified using reverse phase chromatography, a $2^{nd}$ anion exchange chromatography, size exclusion chromatography, and/or hydroxyapatite chromatography to achieve high purity, wherein the level of aggregates is lower than 0.5%, preferably <0.2%, and further preferably <0.1%.

Example 2

Production of EpoR Agonist Peptide-Fc Fusion Protein

DNA for a GGTYSCHFGPLTBVCRPQGG-Linker-feline IgG1a Fc fusion protein SEQ ID NO: 16) is synthesized and cloned into a bacterial expression vector. The complete expression construct comprising the GGTYSCHFGPLTBVCRPQGG-Linker-feline IgG1a Fc fusion protein (SEQ ID NO: 16) gene is confirmed by DNA sequencing. The expression construct was amplified by transforming into DH10B *E. coli* and culturing the cells overnight. DNA for the expression construct was prepared and purified by endo-free plasmid kit (from QIAGEN®). Alternatively, the fusion protein is recovered in the insoluble inclusion body (IB). The IB is solubilized and the fusion protein is refolded at pH between 8.0-10.0, preferably 8.5-9.5, at a temperature between 0-8° C.

The expression construct is transfected into $GS^{-/-}$ Chinese hamster ovarian cells (CHO) and stable cell pools are obtained as discussed in Example 1. The GGTYSCHFGPLTBVCRPQGG-Linker-feline IgG1a Fc fusion protein (SEQ ID NO: 16) is expressed, harvested as discussed in Example 1. The harvested GGTYSCHFGPLTBVCRPQGG-Linker-feline IgG1a Fc fusion protein (SEQ ID NO: 16) is purified by chromatography steps including Protein A affinity, ion exchange, hydroxyapatite and/or hydrophobic interaction. The purified bulk is formulated and lyophilized.

Example 3

Analysis of Sialic Acid Content in the Modified Feline EPO

Sialic acid content of recombinant modified feline EPO was determined using the OPD-labeling method as described previously, see, e.g., Anumula, K. R., Rapid quantitative determination of sialic acids in glycoproteins by High-Performance Liquid Chromatography with a sensitive fluorescence detection. Anal. Biochem. 230(1): 24-30 (1995). In brief, sialic acid was detached from purified rhEPO in 0.5 M NaHSO4 for 20 minutes at 80° C., and derivatized with OPD (o-phenylenediamine-2HCl; Sigma) for 40 minutes at 80° C. OPD-labeled sialic acid was separated on a C18 reversed-phase column (Shim-pack CLC-ODS; Shimadzu, Kyoto, Japan) and detected by a fluorescence detector (Model 474; Waters) with wavelengths 230 nm emission and 425 nm excitation.

Example 4

Analysis of Sialylation Profile of N-Linked Glycans from Recombinant Modified Feline EPO To release N-linked glycans, purified modified feline EPO (50 μg) was resuspended in N-glycanase reaction buffer comprising 20 mM sodium phosphate, 0.02% sodium azide, (pH 7.5) containing 0.1% SDS, and 50 mM β-mercaptoethanol. rhEPO was denatured by boiling for 5 minutes, and added with 0.75% NP-40. The mixture was incubated with 2 units N-glycosidase F (Roche) overnight at 3TC, to release N-linked glycans from rhEPO. Peptides and detergents were then removed using GLYCOCLEAN™ R cartridge, and salts were removed using GLYCOCLEAN™ H cartridge (GLYKO®; PROZYME®, Hayward, Calif.). Purified N-linked glycans were derivatized with 2-AB (2-aminobenzamide) using SIGNAL™ labeling kit (GLYKO®), and nonreacted 2-AB reagents were removed using GLYCOCLEAN™ S cartridge. The above procedures were performed following manufacturer's instructions. 2-AB derivatized N-linked glycans from rhEPO were separated according to number of sialic acids using an anion-exchange column (TSKgel DEAE-5PW, 7.5 mm×75 mm; Tosoh, Tokyo, Japan). Eluents and gradient conditions were as described previously (Llop et al. 2007). Samples were eluted over a 35 min linear gradient from 0% (v/v) to 100% (v/v) solvent A (solvent A: 50% 500 mM ammonium formate, pH 4.5. 30% water, and 20% acetonitrile (ACN); solvent B: 80% water, 20% ACN) at a flow rate of 0.4 mL/min at 30° C., and detected by a fluorescence detector (Model 474; Waters) at wavelengths 330 nm emission and 420 nm excitation. Number of sialic acid in each peak was determined by comparison with peaks in standard 2-AB bovine fetuin N-linked glycan library (GLYKO®).

Example 5

Cell-Based Activity Assay: TF-1 Proliferation Assay

Figure 5:
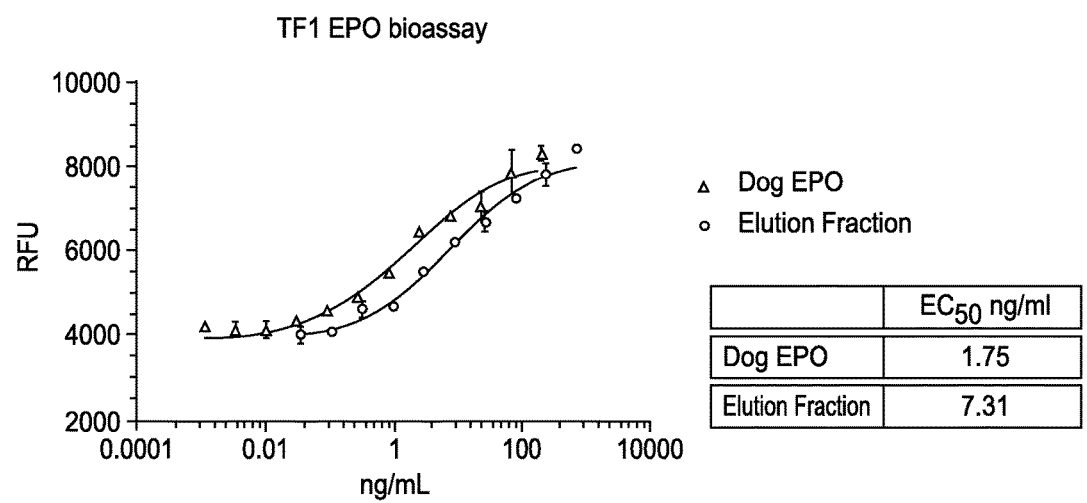
FIG. 5 shows the results of a TF1 EPO bioassay.

Cultured TF-1 cells were maintained in complete medium consisting of RPMI 1640 mediume supplemented with 2 mM L-glutamine, 1% penicillin-streptomycin,n 5% FBS, and recombinant human granulocyte-macrophage colony-stimulating factor at 2 ng/mL. Cells were cultured in a flask and incubated at 37° C. in a humidified incubator with 5% $CO_2$. Diluted recombinant modified feline EPO samples to 2× (200 ng/mL) into 200 mL assay medium in the first well of 96 well plate. Performed serial 2× dilutions for 12 wells (carry 100 μL from first well into 100 μL medium in second well etc.). Assay samples in at least triplicate. Harvested TF-1 cells. Centrifuged at 1200 rpm for 7 minute. Re-suspend cell pellet in 10 mL assay medium. Repeated centrifugation and re-suspension 2 more times to remove growth factor. Diluted cells to 100,000 cells/mL in assay medium. Added 100 μL/well (10,000 cells/well). Cultured for 3 days (37° C., 5% $CO_2$). Add 20 mL/well Alamar Blue. Incubate 6 hours (37° C., 5% $CO_2$). Using microplate reader, measure fluorescence (545 nm excitation, 590 nm emission). FIG. 5 shows the cell-based activity assay data for the Elution Fraction from the Initial Purification of Example 1. A recombinant canine erythropoietin (cEPO) sample from R&D Systems was used as reference for this analysis. As discussed above, this elution pool was expected to contain feline EPO with higher levels (12 or more) of sialic acids. This elution pool showed higher $EC_{50}$ as compared to the reference material dog EPO. This is consistent with prior report, where human EPO analogs with higher levels of glycosylation showed higher EC50 in vitro binding and cell-based activity, see, e.g., Angus M Sinclair: "Erythropoiesis stimulating agents: approaches to modulate activity". Biologics. 2013; 7: 161-174.

Example 6

In Vivo Activity Study

Cats are dosed subcutaneously once per week of the fusion protein at 0.05-0.1 mg/kg or 1 µg/kg of the modified feline EPO for up to 6 weeks. The hematocrits of all cats were determined at baseline and twice weekly thereafter. At the conclusion of the experiment, serum from all animals was collected and assayed for antibodies to the injected product.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A modified non-human mammalian erythropoietin comprising a non-human mammalian erythropoietin modified to have at least one added and/or at least one relocated glycosylation site, wherein said modified non-human mammalian EPO comprises SEQ ID NO:6 wherein Xaa at position 18 is E and Xaa at position 116 is K or absent.

2. The modified non-human mammalian erythropoietin according to claim 1, wherein the at least one added and/or at least one relocated glycosylation site is a site for the attachment of an N-linked carbohydrate chain or a site for the attachment of an O-linked carbohydrate chain.

3. The modified non-human mammalian erythropoietin according to claim 1, wherein the glycosylation site further comprises a fragment of human chorionic gonadotropin, wherein the fragment of human chorionic gonadotropin is SEQ ID NO: 8.

4. A composition comprising
   a) a modified non-human mammalian erythropoietin as defined in claim 1, and
   b) a pharmaceutically acceptable diluent, adjuvant, or carrier.

5. The modified non-human mammalian erythropoietin according to claim 1, wherein Xaa at position 116 is K.

6. A fusion protein, comprising a peptide, a linker and an Fc fragment, wherein:
   a) wherein said peptide comprises SEQ ID NO: 6 wherein Xaa at position 18 is E and Xaa at position 116 is K or absent; and
   b) the Fc fragment has an amino acid sequence comprising SEQ ID NO: 2 or SEQ ID NO: 3 or SEQ ID NO: 4;
   wherein the peptide is fused, through a linker, to the Fc fragment.

7. A composition comprising:
   a) a fusion protein as defined in claim 6, and
   b) a pharmaceutically acceptable diluent, adjuvant, or carrier.

* * * * *

```
                              SEQUENCE LISTING

<160> NUMBER OF SEQ ID NOS: 16

<210> SEQ ID NO 1
<211> LENGTH: 20
<212> TYPE: PRT
<213> ORGANISM: Unknown
<220> FEATURE:
<223> OTHER INFORMATION: Artificial Sequence related to EPOR Agonist
      peptides.
<220> FEATURE:
<221> NAME/KEY: VARIANT
<222> LOCATION: (13)..(13)
<223> OTHER INFORMATION: X at position 13 may be Trp, 1-naphthylalanine,
      or 2-naphthylalanine.

<400> SEQUENCE: 1

Gly Gly Thr Tyr Ser Cys His Phe Gly Pro Leu Thr Xaa Val Cys Arg
1               5                   10                  15

Pro Gln Gly Gly
            20

<210> SEQ ID NO 2
<211> LENGTH: 237
<212> TYPE: PRT
<213> ORGANISM: Felis catus
<220> FEATURE:
<221> NAME/KEY: Variable
<222> LOCATION: (1)..(8)
<223> OTHER INFORMATION: Amino acids 1-8 may be each be present or
      absent.

<400> SEQUENCE: 2

Arg Lys Thr Asp His Pro Pro Gly Pro Lys Pro Cys Asp Cys Pro Lys
1               5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Ser Asp Val Gln Ile Thr
        50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Ala Lys
        115                 120                 125
```

```
Gly Gln Pro His Glu Pro Gln Val Tyr Val Leu Pro Pro Ala Gln Glu
            130                 135                 140

Glu Leu Ser Arg Asn Lys Val Ser Val Thr Cys Leu Ile Lys Ser Phe
145                 150                 155                 160

His Pro Pro Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
                180                 185                 190

Thr Tyr Phe Val Tyr Ser Lys Leu Ser Val Asp Arg Ser His Trp Gln
                195                 200                 205

Arg Gly Asn Thr Tyr Thr Cys Ser Val Ser His Glu Ala Leu His Ser
            210                 215                 220

His His Thr Gln Lys Ser Leu Thr Gln Ser Pro Gly Lys
225                 230                 235

<210> SEQ ID NO 3
<211> LENGTH: 237
<212> TYPE: PRT
<213> ORGANISM: Felis catus
<220> FEATURE:
<221> NAME/KEY: Variable
<222> LOCATION: (1)..(8)
<223> OTHER INFORMATION: Amino Acids 1-8 may each be present or absent.

<400> SEQUENCE: 3

Arg Lys Thr Asp His Pro Pro Gly Pro Lys Pro Cys Asp Cys Pro Lys
1                   5                   10                  15

Cys Pro Pro Pro Glu Met Leu Gly Gly Pro Ser Ile Phe Ile Phe Pro
                20                  25                  30

Pro Lys Pro Lys Asp Thr Leu Ser Ile Ser Arg Thr Pro Glu Val Thr
            35                  40                  45

Cys Leu Val Val Asp Leu Gly Pro Asp Ser Asp Val Gln Ile Thr
 50                  55                  60

Trp Phe Val Asp Asn Thr Gln Val Tyr Thr Ala Lys Thr Ser Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Pro Ile Glu Arg Thr Ile Ser Lys Asp Lys
        115                 120                 125

Gly Gln Pro His Glu Pro Gln Val Tyr Val Leu Pro Pro Ala Gln Glu
            130                 135                 140

Glu Leu Ser Arg Asn Lys Val Ser Val Thr Cys Leu Ile Glu Gly Phe
145                 150                 155                 160

Tyr Pro Ser Asp Ile Ala Val Glu Trp Glu Ile Thr Gly Gln Pro Glu
                165                 170                 175

Pro Glu Asn Asn Tyr Arg Thr Thr Pro Pro Gln Leu Asp Ser Asp Gly
                180                 185                 190

Thr Tyr Phe Leu Tyr Ser Arg Leu Ser Val Asp Arg Ser Arg Trp Gln
                195                 200                 205

Arg Gly Asn Thr Tyr Thr Cys Ser Val Ser His Glu Ala Leu His Ser
            210                 215                 220

His His Thr Gln Lys Ser Leu Thr Gln Ser Pro Gly Lys
225                 230                 235
```

```
<210> SEQ ID NO 4
<211> LENGTH: 237
<212> TYPE: PRT
<213> ORGANISM: Felis catus
<220> FEATURE:
<221> NAME/KEY: Variable
<222> LOCATION: (1)..(8)
<223> OTHER INFORMATION: Amino acids 1-8 each may independently be
      present or absent.

<400> SEQUENCE: 4

Pro Lys Thr Ala Ser Thr Ile Glu Ser Lys Thr Gly Glu Gly Pro Lys
1               5                   10                  15

Cys Pro Val Pro Glu Ile Pro Gly Ala Pro Ser Val Phe Ile Phe Pro
            20                  25                  30

Pro Lys Pro Lys Asp Thr Leu Ser Ile Ser Arg Thr Pro Glu Val Thr
        35                  40                  45

Cys Leu Val Val Asp Leu Gly Pro Asp Asp Ser Asn Val Gln Ile Thr
    50                  55                  60

Trp Phe Val Asp Asn Thr Glu Met His Thr Ala Lys Thr Arg Pro Arg
65                  70                  75                  80

Glu Glu Gln Phe Asn Ser Thr Tyr Arg Val Val Ser Val Leu Pro Ile
                85                  90                  95

Leu His Gln Asp Trp Leu Lys Gly Lys Glu Phe Lys Cys Lys Val Asn
            100                 105                 110

Ser Lys Ser Leu Pro Ser Ala Met Glu Arg Thr Ile Ser Lys Ala Lys
        115                 120                 125

Gly Gln Pro His Glu Pro Gln Val Tyr Val Leu Pro Pro Thr Gln Glu
    130                 135                 140

Glu Leu Ser Glu Asn Lys Val Ser Val Thr Cys Leu Ile Lys Gly Phe
145                 150                 155                 160

His Pro Pro Asp Ile Ala Val Glu Trp Glu Ile Thr Gly Gln Pro Glu
                165                 170                 175

Pro Glu Asn Asn Tyr Gln Thr Thr Pro Pro Gln Leu Asp Ser Asp Gly
            180                 185                 190

Thr Tyr Phe Leu Tyr Ser Arg Leu Ser Val Asp Arg Ser His Trp Gln
        195                 200                 205

Arg Gly Asn Thr Tyr Thr Cys Ser Val Ser His Glu Ala Leu His Ser
    210                 215                 220

His His Thr Gln Lys Ser Leu Thr Gln Ser Pro Gly Lys
225                 230                 235

<210> SEQ ID NO 5
<211> LENGTH: 166
<212> TYPE: PRT
<213> ORGANISM: Felis catus
<220> FEATURE:
<221> NAME/KEY: Variable
<222> LOCATION: (18)..(18)
<223> OTHER INFORMATION: Amino acid at position 18 may be selected from
      E or G.
<220> FEATURE:
<221> NAME/KEY: Variable
<222> LOCATION: (116)..(116)
<223> OTHER INFORMATION: Amino acid at position 116 may be K or absent.

<400> SEQUENCE: 5

Ala Pro Pro Arg Leu Ile Cys Asp Ser Arg Val Leu Glu Arg Tyr Ile
1               5                   10                  15

Leu Xaa Ala Arg Glu Ala Glu Asn Val Thr Met Gly Cys Ala Glu Gly
            20                  25                  30
```

```
Cys Ser Phe Ser Glu Asn Ile Thr Val Pro Asp Thr Lys Val Asn Phe
            35                  40                  45

Tyr Thr Trp Lys Arg Met Asp Val Gly Gln Gln Ala Val Glu Val Trp
 50                  55                  60

Gln Gly Leu Ala Leu Leu Ser Glu Ala Ile Leu Arg Gly Gln Ala Leu
 65                  70                  75                  80

Leu Ala Asn Ser Ser Gln Pro Ser Glu Thr Leu Gln Leu His Val Asp
                 85                  90                  95

Lys Ala Val Ser Ser Leu Arg Ser Leu Thr Ser Leu Leu Arg Ala Leu
                100                 105                 110

Gly Ala Gln Xaa Glu Ala Thr Ser Leu Pro Glu Ala Thr Ser Ala Ala
                115                 120                 125

Pro Leu Arg Thr Phe Thr Val Asp Thr Leu Cys Lys Leu Phe Arg Ile
130                 135                 140

Tyr Ser Asn Phe Leu Arg Gly Lys Leu Thr Leu Tyr Thr Gly Glu Ala
145                 150                 155                 160

Cys Arg Arg Gly Asp Arg
                165
```

<210> SEQ ID NO 6
<211> LENGTH: 166
<212> TYPE: PRT
<213> ORGANISM: Felis catus
<220> FEATURE:
<221> NAME/KEY: Variable
<222> LOCATION: (18)..(18)
<223> OTHER INFORMATION: The amino acid a position 18 may selected from
      E or G.
<220> FEATURE:
<221> NAME/KEY: Variable
<222> LOCATION: (116)..(116)
<223> OTHER INFORMATION: The amino acid a position 116 may be K or
      absent.

<400> SEQUENCE: 6

```
Ala Pro Pro Arg Leu Ile Cys Asp Ser Arg Val Leu Glu Arg Tyr Ile
 1               5                  10                  15

Leu Xaa Ala Arg Glu Ala Glu Asn Val Thr Met Gly Cys Asn Glu Thr
                 20                  25                  30

Cys Ser Phe Ser Glu Asn Ile Thr Val Pro Asp Thr Lys Val Asn Phe
            35                  40                  45

Tyr Thr Trp Lys Arg Met Asp Val Gly Gln Gln Ala Val Glu Val Trp
 50                  55                  60

Gln Gly Leu Ala Leu Leu Ser Glu Ala Ile Leu Arg Gly Gln Ala Leu
 65                  70                  75                  80

Leu Ala Asn Ser Ser Gln Val Asn Glu Thr Leu Gln Leu His Val Asp
                 85                  90                  95

Lys Ala Val Ser Ser Leu Arg Ser Leu Thr Ser Leu Leu Arg Ala Leu
                100                 105                 110

Gly Ala Gln Xaa Glu Ala Thr Ser Leu Pro Glu Ala Thr Ser Ala Ala
                115                 120                 125

Pro Leu Arg Thr Phe Thr Val Asp Thr Leu Cys Lys Leu Phe Arg Ile
130                 135                 140

Tyr Ser Asn Phe Leu Arg Gly Lys Leu Thr Leu Tyr Thr Gly Glu Ala
145                 150                 155                 160

Cys Arg Arg Gly Asp Arg
                165
```

```
<210> SEQ ID NO 7
<211> LENGTH: 5
<212> TYPE: PRT
<213> ORGANISM: Artificial Sequence
<220> FEATURE:
<223> OTHER INFORMATION: Linker sequence.
<220> FEATURE:
<221> NAME/KEY: Repeat
<222> LOCATION: (1)..(5)
<223> OTHER INFORMATION: The sequence may be extended by repetition 2-4
      times.

<400> SEQUENCE: 7

Gly Gly Gly Gly Ser
1               5

<210> SEQ ID NO 8
<211> LENGTH: 28
<212> TYPE: PRT
<213> ORGANISM: Artificial Sequence
<220> FEATURE:
<223> OTHER INFORMATION: Chorionic Gonadotropin fragment.

<400> SEQUENCE: 8

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
                20                  25

<210> SEQ ID NO 9
<211> LENGTH: 27
<212> TYPE: PRT
<213> ORGANISM: Homo sapiens
<220> FEATURE:
<221> NAME/KEY: SIGNAL
<222> LOCATION: (1)..(27)

<400> SEQUENCE: 9

Met Gly Val His Glu Cys Pro Ala Trp Leu Trp Leu Leu Ser Leu
1               5                   10                  15

Leu Ser Leu Pro Leu Gly Leu Pro Val Leu Gly
                20                  25

<210> SEQ ID NO 10
<211> LENGTH: 166
<212> TYPE: PRT
<213> ORGANISM: Canis familiaris

<400> SEQUENCE: 10

Ala Pro Pro Arg Leu Ile Cys Asp Ser Arg Val Leu Glu Arg Tyr Ile
1               5                   10                  15

Leu Glu Ala Arg Glu Ala Glu Asn Val Thr Met Gly Cys Ala Gln Gly
                20                  25                  30

Cys Ser Phe Ser Glu Asn Ile Thr Val Pro Asp Thr Lys Val Asn Phe
            35                  40                  45

Tyr Thr Trp Lys Arg Met Asp Val Gly Gln Gln Ala Leu Glu Val Trp
        50                  55                  60

Gln Gly Leu Ala Leu Leu Ser Glu Ala Ile Leu Arg Gly Gln Ala Leu
65                  70                  75                  80

Leu Ala Asn Ala Ser Gln Pro Ser Glu Thr Pro Gln Leu His Val Asp
                85                  90                  95

Lys Ala Val Ser Ser Leu Arg Ser Leu Thr Ser Leu Leu Arg Ala Leu
                100                 105                 110
```

```
Gly Ala Gln Lys Glu Ala Met Ser Leu Pro Glu Ala Ser Pro Ala
        115                 120                 125

Pro Leu Arg Thr Phe Thr Val Asp Thr Leu Cys Lys Leu Phe Arg Ile
130                 135                 140

Tyr Ser Asn Phe Leu Arg Gly Lys Leu Thr Leu Tyr Thr Gly Glu Ala
145                 150                 155                 160

Cys Arg Arg Gly Asp Arg
                165
```

<210> SEQ ID NO 11
<211> LENGTH: 192
<212> TYPE: PRT
<213> ORGANISM: Canis familiaris

<400> SEQUENCE: 11

```
Met Gly Ala Cys Glu Cys Pro Ala Leu Phe Leu Leu Leu Ser Leu Leu
1               5                   10                  15

Leu Leu Pro Leu Gly Leu Pro Val Leu Gly Ala Pro Arg Leu Ile
            20                  25                  30

Cys Asp Ser Arg Val Leu Glu Arg Tyr Ile Leu Glu Ala Arg Glu Ala
        35                  40                  45

Glu Asn Val Thr Met Gly Cys Ala Gln Gly Cys Ser Phe Ser Glu Asn
    50                  55                  60

Ile Thr Val Pro Asp Thr Lys Val Asn Phe Tyr Thr Trp Lys Arg Met
65                  70                  75                  80

Asp Val Gly Gln Gln Ala Leu Glu Val Trp Gln Gly Leu Ala Leu Leu
                85                  90                  95

Ser Glu Ala Ile Leu Arg Gly Gln Ala Leu Leu Ala Asn Ala Ser Gln
            100                 105                 110

Pro Ser Glu Thr Pro Gln Leu His Val Asp Lys Ala Val Ser Ser Leu
        115                 120                 125

Arg Ser Leu Thr Ser Leu Leu Arg Ala Leu Gly Ala Gln Lys Glu Ala
    130                 135                 140

Met Ser Leu Pro Glu Glu Ala Ser Pro Ala Pro Leu Arg Thr Phe Thr
145                 150                 155                 160

Val Asp Thr Leu Cys Lys Leu Phe Arg Ile Tyr Ser Asn Phe Leu Arg
                165                 170                 175

Gly Lys Leu Thr Leu Tyr Thr Gly Glu Ala Cys Arg Arg Gly Asp Arg
            180                 185                 190
```

<210> SEQ ID NO 12
<211> LENGTH: 26
<212> TYPE: PRT
<213> ORGANISM: Felis catus
<220> FEATURE:
<221> NAME/KEY: SIGNAL
<222> LOCATION: (1)..(26)

<400> SEQUENCE: 12

```
Met Gly Ser Cys Glu Cys Pro Ala Leu Leu Leu Leu Ser Leu Leu
1               5                   10                  15

Leu Leu Pro Leu Gly Leu Pro Val Leu Gly
            20                  25
```

<210> SEQ ID NO 13
<211> LENGTH: 40
<212> TYPE: PRT
<213> ORGANISM: Canis familiaris

```
<220> FEATURE:
<221> NAME/KEY: SIGNAL
<222> LOCATION: (1)..(40)

<400> SEQUENCE: 13

Met Cys Glu Pro Ala Pro Pro Lys Pro Thr Gln Ser Ala Trp His Ser
1               5                   10                  15

Phe Pro Glu Cys Pro Ala Leu Leu Leu Leu Ser Leu Leu Leu
            20                  25                  30

Pro Leu Gly Leu Pro Val Leu Gly
        35                  40

<210> SEQ ID NO 14
<211> LENGTH: 593
<212> TYPE: DNA
<213> ORGANISM: Artificial Sequence
<220> FEATURE:
<223> OTHER INFORMATION: DNA sequence for Modified Feline EPO including
      5'-Hind III and 3'-Pac I restriction endonuclease cleavage sites

<400> SEQUENCE: 14
aagcttatgg gttcctgtga atgccctgcc ctcctcctcc tgctgtccct gttgttgctc      60
cccctcggac tcccggtcct gggcgcgccc ccaagactga tctgcgattc acgcgtgctg     120
gagcggtaca ttcttgaggc tcgggaagcc gagaacgtga ccatgggttg taacgagact     180
tgctcgttct ccgaaaacat taccgtgccg gacaccaagg tcaacttcta cacctggaaa     240
cggatggacg tgggacagca agccgtggaa gtgtggcagg ggcttgccct gctgtccgag     300
gccatcctgc gcggccaggc cctgctggcc aactcaagcc aggtcaacga gactctgcaa     360
cttcacgtgg ataaggccgt gtcgagcctg aggagcctca cctcgctcct gcgggcactg     420
ggagcccaga aggaagccac ttccctgcct gaagcaacat ccgctgcgcc gctgaggacc     480
tttactgtgg acacgctgtg caagctgttc cgcatctact ccaatttcct gcgggggaag     540
ctgaccttgt ataccggaga agcgtgccgc agaggcgaca gatagttaat taa            593

<210> SEQ ID NO 15
<211> LENGTH: 4
<212> TYPE: PRT
<213> ORGANISM: Artificial sequence
<220> FEATURE:
<223> OTHER INFORMATION: shortened version of a FLAG tag

<400> SEQUENCE: 15

Asp Tyr Lys Asp
1

<210> SEQ ID NO 16
<211> LENGTH: 20
<212> TYPE: PRT
<213> ORGANISM: Artificial sequence
<220> FEATURE:
<223> OTHER INFORMATION: Linker-feline IgG1a Fc fusion protein

<400> SEQUENCE: 16

Gly Gly Thr Tyr Ser Cys His Phe Gly Pro Leu Thr Asx Val Cys Arg
1               5                   10                  15

Pro Gln Gly Gly
        20
```